US011478616B2

(12) United States Patent
Andino et al.

(10) Patent No.: US 11,478,616 B2
(45) Date of Patent: *Oct. 25, 2022

(54) SECUREMENT DEVICE HAVING AN INTEGRAL STRAP AND DRESSING

(71) Applicant: C. R. Bard, Inc., Franklin Lakes, NJ (US)

(72) Inventors: Rafael V. Andino, Grayson, GA (US); Christopher J. Brooks, Huntington, NY (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 115 days.

This patent is subject to a terminal disclaimer.

(21) Appl. No.: 16/913,999

(22) Filed: Jun. 26, 2020

(65) Prior Publication Data
US 2020/0324085 A1 Oct. 15, 2020

Related U.S. Application Data

(63) Continuation of application No. 14/764,979, filed as application No. PCT/US2014/020207 on Mar. 4, 2014, now Pat. No. 10,729,887.
(Continued)

(51) Int. Cl.
*A61M 25/02* (2006.01)

(52) U.S. Cl.
CPC ....... *A61M 25/02* (2013.01); *A61M 2025/024* (2013.01); *A61M 2025/028* (2013.01);
(Continued)

(58) Field of Classification Search
CPC ............ A61M 25/02; A61M 2025/024; A61M 2025/0246; A61M 2025/0253; A61M 2025/0266; A61M 2025/028

See application file for complete search history.

(56) References Cited

U.S. PATENT DOCUMENTS 2,525,398 A  10/1950 Collins
2,533,961 A  12/1950 Rousseau et al.
(Continued)

FOREIGN PATENT DOCUMENTS

CA  995995 A1  8/1976
CA  2281457 A1  2/2001
(Continued)

OTHER PUBLICATIONS

U.S. Appl. No. 14/764,979, filed Jul. 30, 2015 Notice of Allowance dated Apr. 15, 2020.
(Continued)

*Primary Examiner* — Jenna Zhang
(74) *Attorney, Agent, or Firm* — Rutan & Tucker LLP

(57) ABSTRACT

A securement device for securing a catheter includes a retainer, a strap, a first anchor pad and a second anchor pad, a gap separating an edge of the first anchor pad from an adjacent edge of the second anchor pad. The retainer can include a first base member secured to an upper surface of the first anchor pad, a second base member secured to an upper surface of the second anchor pad, and a body coupled to the first and second base members. The body can include a portion spanning the gap separating the first anchor pad from the second anchor pad. The portion of the body can include an open channel through an upper surface of the body, the open channel aligned with the gap. The body can further include a first securement mechanism and a second securement mechanism. The strap can be rotatably coupled to the body.

20 Claims, 16 Drawing Sheets

Related U.S. Application Data

(60) Provisional application No. 61/789,412, filed on Mar. 15, 2013.

(52) U.S. Cl.
CPC .......... *A61M 2025/0246* (2013.01); *A61M 2025/0253* (2013.01); *A61M 2025/0266* (2013.01)

(56) References Cited

U.S. PATENT DOCUMENTS

| | | |
|---|---|---|
| 2,707,953 A | 5/1955 | Ryan |
| 2,893,671 A | 7/1959 | Flora et al. |
| 3,059,645 A | 10/1962 | Hasbrouck et al. |
| 3,064,648 A | 11/1962 | Bujan |
| 3,167,072 A | 1/1965 | Stone et al. |
| 3,482,569 A | 12/1969 | Raaelli, Sr. |
| 3,529,597 A | 9/1970 | Fuzak |
| 3,602,227 A | 8/1971 | Andrew |
| 3,630,195 A | 12/1971 | Santomieri |
| 3,677,250 A | 7/1972 | Thomas |
| 3,766,915 A | 10/1973 | Rychlik |
| 3,834,380 A | 9/1974 | Boyd |
| 3,847,370 A | 11/1974 | Engelsher |
| 3,856,020 A | 12/1974 | Kovac |
| 3,896,527 A | 7/1975 | Miller et al. |
| 3,900,026 A | 8/1975 | Wagner |
| 3,905,322 A | 9/1975 | Peterman et al. |
| 3,906,592 A | 9/1975 | Sakasegawa et al. |
| 3,906,946 A | 9/1975 | Nordstrom |
| 3,934,576 A | 1/1976 | Danielsson |
| 3,942,228 A | 3/1976 | Buckman et al. |
| 3,973,565 A | 8/1976 | Steer |
| 3,993,081 A | 11/1976 | Cussell |
| 4,020,835 A | 5/1977 | Nordstrom et al. |
| 4,030,540 A | 6/1977 | Roma |
| 4,057,066 A | 11/1977 | Taylor |
| 4,059,105 A | 11/1977 | Cutruzzula et al. |
| 4,082,094 A | 4/1978 | Dailey |
| 4,114,618 A | 9/1978 | Vargas |
| 4,129,128 A | 12/1978 | McFarlane |
| 4,133,307 A | 1/1979 | Ness |
| 4,142,527 A | 3/1979 | Garcia |
| 4,149,539 A | 4/1979 | Cianci |
| 4,161,177 A | 7/1979 | Fuchs |
| 4,170,995 A | 10/1979 | Levine et al. |
| 4,193,174 A | 3/1980 | Stephens |
| 4,209,015 A | 6/1980 | Wicks |
| 4,224,937 A | 9/1980 | Gordon |
| 4,248,229 A | 2/1981 | Miller |
| 4,250,880 A | 2/1981 | Gordon |
| 4,316,461 A | 2/1982 | Marais et al. |
| 4,324,236 A | 4/1982 | Gordon et al. |
| 4,326,519 A | 4/1982 | D'Alo et al. |
| 4,333,468 A | 6/1982 | Geist |
| 4,356,599 A | 11/1982 | Larson et al. |
| 4,362,156 A | 12/1982 | Feller, Jr. et al. |
| 4,392,853 A | 7/1983 | Muto |
| 4,397,647 A | 8/1983 | Gordon |
| 4,402,691 A | 9/1983 | Rosenthal et al. |
| 4,405,163 A | 9/1983 | Voges et al. |
| 4,405,312 A | 9/1983 | Gross et al. |
| 4,442,994 A | 4/1984 | Logsdon |
| 4,449,975 A | 5/1984 | Perry |
| 4,453,933 A | 6/1984 | Speaker |
| 4,474,559 A | 10/1984 | Steiger |
| 4,480,639 A | 11/1984 | Peterson et al. |
| 4,484,913 A | 11/1984 | Swauger |
| 4,498,903 A | 2/1985 | Mathew |
| 4,516,968 A | 5/1985 | Marshall et al. |
| 4,517,971 A | 5/1985 | Sorbonne |
| 4,563,177 A | 1/1986 | Kamen |
| 4,583,976 A | 4/1986 | Ferguson |
| 4,623,102 A | 11/1986 | Hough, Jr. |
| 4,633,863 A | 1/1987 | Filips et al. |
| 4,650,473 A | 3/1987 | Bartholomew et al. |
| 4,659,329 A | 4/1987 | Annis |
| 4,660,555 A | 4/1987 | Payton |
| 4,711,636 A | 12/1987 | Bierman |
| 4,726,716 A | 2/1988 | McGuire |
| 4,733,666 A | 3/1988 | Mercer, Jr. |
| 4,742,824 A | 5/1988 | Payton et al. |
| 4,762,513 A | 8/1988 | Choy et al. |
| 4,775,121 A | 10/1988 | Carty |
| 4,808,162 A | 2/1989 | Oliver |
| 4,823,789 A | 4/1989 | Beisang, III |
| 4,826,466 A | 5/1989 | Friquet |
| 4,826,486 A | 5/1989 | Palsrok et al. |
| 4,838,878 A | 6/1989 | Kalt et al. |
| 4,852,844 A | 8/1989 | Villaveces |
| 4,857,058 A | 8/1989 | Payton Hugh W. |
| 4,863,432 A | 9/1989 | Kvalo |
| 4,869,465 A | 9/1989 | Yirmiyahu et al. |
| 4,880,412 A | 11/1989 | Weiss |
| 4,896,465 A | 1/1990 | Rhodes et al. |
| 4,897,082 A | 1/1990 | Erskine |
| 4,898,587 A | 2/1990 | Mera |
| 4,919,654 A | 4/1990 | Kalt |
| 4,932,943 A | 6/1990 | Nowak |
| 4,944,728 A | 7/1990 | Carrell et al. |
| 4,952,207 A | 8/1990 | Lemieux |
| 4,955,864 A | 9/1990 | Hajduch |
| 4,976,700 A | 12/1990 | Tollini |
| 4,981,475 A | 1/1991 | Haindl |
| 4,997,421 A | 3/1991 | Palsrok et al. |
| 5,000,741 A | 3/1991 | Kalt |
| 5,037,397 A | 8/1991 | Kalt et al. |
| 5,073,166 A | 12/1991 | Parks et al. |
| 5,073,170 A | 12/1991 | Schneider |
| 5,084,026 A | 1/1992 | Shapiro |
| 5,098,399 A | 3/1992 | Tollini |
| 5,100,393 A | 3/1992 | Johnson |
| 5,112,313 A | 5/1992 | Sallee |
| 5,137,519 A | 8/1992 | Littrell et al. |
| 5,147,322 A | 9/1992 | Bowen et al. |
| 5,156,641 A | 10/1992 | White |
| 5,188,609 A | 2/1993 | Bayless et al. |
| 5,192,273 A | 3/1993 | Bierman |
| 5,192,274 A | 3/1993 | Bierman |
| 5,195,981 A | 3/1993 | Johnson |
| 5,210,913 A | 5/1993 | Clark |
| 5,226,892 A | 7/1993 | Boswell |
| 5,234,185 A | 8/1993 | Hoffman et al. |
| 5,248,306 A | 9/1993 | Clark et al. |
| 5,263,943 A | 11/1993 | Vanderbrook |
| 5,266,401 A | 11/1993 | Tollini |
| 5,267,967 A | 12/1993 | Schneider |
| 5,282,463 A | 2/1994 | Hammersley |
| 5,292,312 A | 3/1994 | Delk et al. |
| 5,304,146 A | 4/1994 | Johnson et al. |
| 5,306,243 A | 4/1994 | Bonaldo |
| 5,306,256 A | 4/1994 | Jose |
| 5,308,337 A | 5/1994 | Bingisser |
| 5,314,411 A | 5/1994 | Bierman et al. |
| 5,322,514 A | 6/1994 | Steube et al. |
| 5,330,438 A | 7/1994 | Gollobin et al. |
| 5,334,186 A | 8/1994 | Alexander |
| 5,336,195 A | 8/1994 | Daneshvar |
| 5,338,308 A | 8/1994 | Wilk |
| 5,342,317 A | 8/1994 | Claywell |
| 5,344,406 A | 9/1994 | Spooner |
| 5,344,414 A | 9/1994 | Lopez et al. |
| 5,346,479 A | 9/1994 | Schneider |
| 5,352,211 A | 10/1994 | Merskelly |
| 5,354,282 A | 10/1994 | Bierman |
| 5,354,283 A | 10/1994 | Bark et al. |
| 5,368,575 A | 11/1994 | Chang |
| 5,380,293 A | 1/1995 | Grant |
| 5,380,294 A | 1/1995 | Persson |
| 5,380,301 A | 1/1995 | Prichard et al. |
| 5,382,239 A | 1/1995 | Orr et al. |
| 5,382,240 A | 1/1995 | Lam |
| 5,389,082 A | 2/1995 | Baugues et al. |

(56) References Cited

U.S. PATENT DOCUMENTS

| | | | |
|---|---|---|---|
| 5,395,344 A | 3/1995 | Beisang, III et al. |
| 5,398,679 A | 3/1995 | Freed |
| 5,403,285 A | 4/1995 | Roberts |
| 5,413,562 A | 5/1995 | Swauger |
| 5,431,695 A | 7/1995 | Wiklund et al. |
| 5,443,460 A | 8/1995 | Miklusek |
| 5,449,349 A | 9/1995 | Sallee et al. |
| 5,456,671 A | 10/1995 | Bierman |
| 5,468,228 A | 11/1995 | Gebert |
| 5,468,230 A | 11/1995 | Corn |
| 5,468,231 A | 11/1995 | Newman et al. |
| 5,470,321 A | 11/1995 | Forster et al. |
| D364,922 S | 12/1995 | Bierman |
| 5,484,420 A | 1/1996 | Russo |
| 5,494,245 A | 2/1996 | Suzuki et al. |
| 5,496,282 A | 3/1996 | Militzer et al. |
| 5,496,283 A | 3/1996 | Alexander |
| 5,499,976 A | 3/1996 | Dalton |
| 5,520,656 A | 5/1996 | Byrd |
| 5,522,803 A | 6/1996 | Teissen-Simony |
| 5,527,293 A | 6/1996 | Zamierowski |
| 5,531,695 A | 7/1996 | Swisher |
| 5,549,567 A | 8/1996 | Wolman |
| D375,355 S | 11/1996 | Bierman |
| 5,578,013 A | 11/1996 | Bierman |
| 5,626,565 A | 5/1997 | Landis et al. |
| 5,632,274 A | 5/1997 | Quedens et al. |
| 5,637,098 A | 6/1997 | Bierman |
| 5,638,814 A | 6/1997 | Byrd |
| 5,643,217 A | 7/1997 | Dobkin |
| 5,672,159 A | 9/1997 | Warrick |
| 5,681,290 A | 10/1997 | Alexander |
| 5,685,859 A | 11/1997 | Kornerup |
| 5,686,096 A | 11/1997 | Khan et al. |
| 5,690,617 A | 11/1997 | Wright |
| 5,693,032 A | 12/1997 | Bierman |
| 5,697,907 A | 12/1997 | Gaba |
| 5,702,371 A | 12/1997 | Bierman |
| D389,911 S | 1/1998 | Bierman |
| 5,709,665 A | 1/1998 | Vergano et al. |
| 5,722,959 A | 3/1998 | Bierman |
| 5,738,660 A | 4/1998 | Luther |
| 5,755,225 A | 5/1998 | Hutson |
| 5,795,335 A | 8/1998 | Zinreich |
| 5,800,402 A | 9/1998 | Bierman |
| 5,810,781 A | 9/1998 | Bierman |
| 5,810,835 A | 9/1998 | Ryan et al. |
| 5,827,230 A | 10/1998 | Bierman |
| 5,827,239 A | 10/1998 | Dillon et al. |
| 5,833,667 A | 11/1998 | Bierman |
| 5,846,255 A | 12/1998 | Casey |
| 5,916,199 A | 6/1999 | Miles |
| 5,944,696 A | 8/1999 | Bayless et al. |
| 5,989,213 A | 11/1999 | Maginot |
| 6,001,081 A | 12/1999 | Collen |
| 6,015,119 A | 1/2000 | Starchevich |
| 6,027,480 A | 2/2000 | Davis et al. |
| 6,074,368 A | 6/2000 | Wright |
| 6,113,577 A | 9/2000 | Hakky et al. |
| 6,132,398 A | 10/2000 | Bierman |
| 6,139,532 A | 10/2000 | Howell et al. |
| 6,206,897 B1 | 3/2001 | Jamiolkowski et al. |
| 6,213,979 B1 | 4/2001 | Bierman |
| 6,224,571 B1 | 5/2001 | Bierman |
| 6,228,064 B1 | 5/2001 | Abita et al. |
| 6,231,548 B1 | 5/2001 | Bassett |
| 6,273,873 B1 | 8/2001 | Fleischer |
| 6,283,945 B1 | 9/2001 | Bierman |
| 6,290,265 B1 | 9/2001 | Warburton-Pitt et al. |
| 6,290,676 B1 | 9/2001 | Bierman |
| 6,311,933 B1 | 11/2001 | Starchevich |
| 6,332,874 B1 | 12/2001 | Eliasen et al. |
| 6,361,523 B1 | 3/2002 | Bierman |
| 6,387,075 B1 | 5/2002 | Stivland et al. |
| 6,387,076 B1 * | 5/2002 | Landuyt | A61M 25/02 |
| | | | 604/174 |
| 6,413,240 B1 | 7/2002 | Bierman et al. |
| 6,428,513 B1 | 8/2002 | Abrahamson |
| 6,428,514 B1 | 8/2002 | Goebel et al. |
| 6,428,516 B1 | 8/2002 | Bierman |
| 6,447,485 B2 | 9/2002 | Bierman |
| 6,447,486 B1 | 9/2002 | Tollini |
| 6,458,104 B2 | 10/2002 | Gautsche |
| 6,482,183 B1 | 11/2002 | Pausch et al. |
| 6,488,664 B1 | 12/2002 | Solomon et al. |
| 6,491,713 B1 | 12/2002 | Deininger et al. |
| 6,500,154 B1 | 12/2002 | Hakky et al. |
| 6,572,587 B2 | 6/2003 | Lerman et al. |
| 6,572,588 B1 | 6/2003 | Bierman et al. |
| 6,582,403 B1 | 6/2003 | Bierman et al. |
| 6,585,703 B1 | 7/2003 | Kassel et al. |
| 6,631,715 B2 | 10/2003 | Kim |
| 6,663,600 B2 | 12/2003 | Bierman et al. |
| 6,786,892 B2 | 9/2004 | Bierman |
| 6,824,527 B2 | 11/2004 | Gollobin |
| 6,837,875 B1 | 1/2005 | Bierman |
| 6,841,715 B2 | 1/2005 | Roberts |
| 6,872,194 B2 | 3/2005 | Doyle et al. |
| 6,929,625 B2 | 8/2005 | Bierman |
| 6,951,550 B2 | 10/2005 | Bierman |
| 6,972,003 B2 | 12/2005 | Bierman et al. |
| 6,979,320 B2 | 12/2005 | Bierman |
| 6,984,145 B1 | 1/2006 | Lim |
| 7,018,362 B2 | 3/2006 | Bierman et al. |
| 7,137,968 B1 | 11/2006 | Burrell et al. |
| D533,442 S | 12/2006 | Baylor |
| 7,175,615 B2 | 2/2007 | Hanly et al. |
| 7,247,150 B2 | 7/2007 | Bierman |
| 7,294,752 B1 | 11/2007 | Propp |
| D593,680 S | 6/2009 | Hafele et al. |
| 7,563,251 B2 | 7/2009 | Bierman et al. |
| 7,704,260 B2 | 4/2010 | Skakoon et al. |
| 7,776,003 B2 | 8/2010 | Zauner |
| 7,785,295 B2 | 8/2010 | Bierman |
| 8,016,792 B2 | 9/2011 | Wright et al. |
| 8,366,678 B2 | 2/2013 | Bierman et al. |
| 8,419,689 B2 | 4/2013 | Fink et al. |
| 8,728,039 B2 | 5/2014 | Bierman et al. |
| 9,138,560 B2 | 9/2015 | Wright et al. |
| 9,468,740 B2 | 10/2016 | Bierman et al. |
| 9,480,821 B2 | 11/2016 | Ciccone et al. |
| 9,974,929 B2 | 5/2018 | Ciccone et al. |
| 10,537,714 B2 | 1/2020 | Andino et al. |
| 2002/0068904 A1 | 6/2002 | Bierman et al. |
| 2002/0165493 A1 | 11/2002 | Bierman |
| 2003/0229313 A1 | 12/2003 | Bierman |
| 2004/0034330 A1 | 2/2004 | Bierman et al. |
| 2005/0096606 A1 | 5/2005 | Millerd |
| 2005/0113759 A1 | 5/2005 | Mueller et al. |
| 2005/0192539 A1 | 9/2005 | Bierman et al. |
| 2005/0197628 A1 | 9/2005 | Roberts et al. |
| 2006/0089600 A1 | 4/2006 | Bierman et al. |
| 2006/0129103 A1 | 6/2006 | Bierman et al. |
| 2006/0135944 A1 | 6/2006 | Bierman |
| 2007/0043326 A1 * | 2/2007 | Navarro | A61M 25/02 |
| | | | 604/264 |
| 2007/0142782 A2 | 6/2007 | Bierman |
| 2007/0219500 A1 | 9/2007 | Wright et al. |
| 2007/0276335 A1 | 11/2007 | Bierman |
| 2008/0132848 A1 * | 6/2008 | Wright | A61M 25/01 |
| | | | 604/174 |
| 2008/0200880 A1 | 8/2008 | Kyvik et al. |
| 2009/0143740 A1 | 6/2009 | Bierman et al. |
| 2009/0143741 A1 | 6/2009 | Burn |
| 2009/0209906 A1 | 8/2009 | Tanaka et al. |
| 2010/0100049 A1 | 4/2010 | Godfrey |
| 2010/0324491 A1 * | 12/2010 | Bierman | A61M 25/02 |
| | | | 604/174 |
| 2012/0123343 A1 | 5/2012 | Aviles |
| 2012/0135314 A1 * | 5/2012 | Shim | H01M 10/052 |
| | | | 429/341 |
| 2012/0136314 A1 * | 5/2012 | Ciccone | A61M 25/02 |
| | | | 604/174 |

(56) References Cited

U.S. PATENT DOCUMENTS

| | | | |
|---|---|---|---|
| 2012/0143140 A1 | 6/2012 | Bierman et al. | |
| 2012/0271240 A1* | 10/2012 | Andino | A61M 25/02 604/180 |
| 2013/0053785 A1* | 2/2013 | Parvatiyar | A61M 25/02 604/174 |
| 2014/0343501 A1 | 11/2014 | Bierman et al. | |
| 2017/0043131 A1 | 2/2017 | Ciccone et al. | |

FOREIGN PATENT DOCUMENTS

| | | |
|---|---|---|
| CA | 2483995 A1 | 4/2004 |
| DE | 2341297 A1 | 4/1975 |
| EP | 0064284 A2 | 11/1982 |
| EP | 0247590 A2 | 12/1987 |
| EP | 0356683 A1 | 3/1990 |
| EP | 0440101 A2 | 8/1991 |
| EP | 0567029 A1 | 10/1993 |
| EP | 0931560 A1 | 7/1999 |
| EP | 2968850 A1 | 1/2016 |
| EP | 2968850 B1 | 2/2019 |
| FR | 1184139 A | 7/1959 |
| FR | 2381529 A1 | 9/1978 |
| FR | 2852520 A1 | 9/2004 |
| GB | 2063679 A | 6/1981 |
| GB | 2086466 A | 5/1982 |
| GB | 2288542 A | 10/1995 |
| GB | 2333234 A | 7/1999 |
| GB | 2344054 A | 5/2000 |
| JP | S60-051377 | 4/1985 |
| JP | 01308572 | 12/1989 |
| JP | H04-037448 | 3/1992 |
| JP | 1994-344852 A | 12/1994 |
| JP | 1995-028563 | 5/1995 |
| JP | H08-257138 A | 10/1996 |
| JP | 2005-535432 A | 11/2005 |
| JP | 04-051767 B2 | 2/2008 |
| JP | 2009-507533 A | 2/2009 |
| WO | 8001458 A1 | 7/1980 |
| WO | 8502774 A1 | 7/1985 |
| WO | 9116939 A1 | 11/1991 |
| WO | 9219309 A1 | 11/1992 |
| WO | 9610435 A1 | 4/1996 |
| WO | 1996/026756 A1 | 9/1996 |
| WO | 9853872 A1 | 12/1998 |
| WO | 9902399 A1 | 1/1999 |
| WO | 1999/020334 A1 | 4/1999 |
| WO | 9955409 A1 | 11/1999 |
| WO | 2001/068180 A1 | 9/2001 |
| WO | 2004016309 A2 | 2/2004 |
| WO | 2006/113620 A2 | 10/2006 |
| WO | 2007028007 A2 | 3/2007 |
| WO | 2008051810 A2 | 5/2008 |
| WO | 2011/060197 A1 | 5/2011 |

OTHER PUBLICATIONS

U.S. Appl. No. 14/859,090, filed Sep. 18, 2015 Non-Final Office Action dated Apr. 7, 2016.
U.S. Appl. No. 14/859,090, filed Sep. 18, 2015 Noticeof Allowance dated Sep. 27, 2016.
U.S. Appl. No. 15/336,537, filed Oct. 27, 2016 Final Office Action dated Nov. 14, 2017.
U.S. Appl. No. 15/336,537, filed Oct. 27, 2016 Non-Final Office Action dated Jun. 9, 2017.
AU 2014237929 filed Jul. 9, 2015 Examination Report dated Feb. 9, 2018.
AU 2014237929 filed Jul. 9, 2015 Examination Report dated May 11, 2018.
CN 201480015384.2 filed Sep. 14, 2015 Office Action dated Feb. 5, 2018.
CN 201480015384.2 filed Sep. 14, 2015 Office Action dated Mar. 27, 2019.
CN 201480015384.2 filed Sep. 14, 2015 Office Action dated Oct. 31, 2018.
EP 14770518.0 filed Sep. 7, 2015 Extended European Search Report, dated Aug. 23, 2016.
EP 14770518.0 filed Sep. 7, 2015 Intent to Grant, dated Sep. 27, 2018.
EP 14770518.0 filed Sep. 7, 2015 Office Action, dated Apr. 24, 2018.
EP 14770518.0 filed Sep. 7, 2015 Office Action, dated Jul. 4, 2017.
EP 14770518.0 filed Sep. 7, 2015 Office Action, dated Nov. 20, 2017.
EP07717867.1 filed Aug. 4, 2008 Office Action dated Aug. 21, 2018.
EP07717867.1 filed Aug. 4, 2008 Office Action dated May 17, 2019.
EP07717867.1 filed Aug. 4, 2008 Supplemental European Search Report dated Oct. 4, 2010.
Extended European Search Report for EP 07 71 7867, PCT/US2007/000969, dated Oct. 14, 2010.
JP 2016-500588 filed Sep. 11, 2015 Office Action dated Apr. 25, 2018.
JP 2016-500588 filed Sep. 11, 2015 Office Action dated Dec. 27, 2017.
Medtronic. Intracranial Pressure Monitoring: A Handbook for the Nursing Professional. (2000).
Multiple-Lumen Central Venous Catheterization Product With ARROW+gard.™. Antiseptic Surface (Arrow International brochure) (Apr. 1994).
PCT/US07/00969 filed Jan. 11, 2007, International Search Report and Written Opinion, dated Sep. 25, 2007.
PCT/US07/00969 filed Nov. 1, 2007 International Search Report dated Sep. 25, 2007.
PCT/US07/00969 filed Nov. 1, 2007 Written Opinion dated Sep. 25, 2007.
PCT/US07/84346 filed Nov. 9, 2007 International Search Report and Written Opinion dated Oct. 31, 2008.
PCT/US08/68854 filed Jun. 30, 2008 International Search Report dated Sep. 3, 2008.
PCT/US08/68854 filed Jun. 30, 2008 Written Opinion dated Sep. 5, 2008.
PCT/US10/56421 filed Nov. 11, 2010 International Search Report and Written Opinion dated Jan. 12, 2011.
PCT/US2001/006836 filed Feb. 3, 2001 International Search Report dated Aug. 2, 2001.
PCT/US2008/068854 filed Jun. 30, 2008 International Preliminary Report dated Sep. 5, 2008.
PCT/US2014/020207 filed Mar. 4, 2014 International Search Report and Written Opinion dated Jun. 12, 2014.
Photographs (4) of Catheter Clamp and Rigid Fastener sold by Arrow International. Inc. (2009).
Search Result, Percufix® Catheter Cuff Kit, downloaded from the Internet on Aug. 15, 2001.
U.S. Appl. No. 11/690,101, filed Mar. 22, 2007 Advisory Action dated Dec. 3, 2014.
U.S. Appl. No. 11/690,101, filed Mar. 22, 2007 Final Office Action dated Sep. 25, 2014.
U.S. Appl. No. 13/001,924, filed Jan. 30, 2012 Advisory Action dated Jun. 25, 2015.
U.S. Appl. No. 13/001,924, filed Jan. 30, 2012 Non-Final Office Action dated Mar. 28, 2016.
U.S. Appl. No. 13/500,853, filed Jul. 13, 2012 Examiner's Answer to Appeal Brief dated Dec. 20, 2016.
U.S. Appl. No. 13/500,853, filed Jul. 13, 2012 Final Office Action dated Apr. 12, 2016.
U.S. Appl. No. 13/500,853, filed Jul. 13, 2012 Non-Final Office Action dated Aug. 21, 2014.
U.S. Appl. No. 13/500,853, filed Jul. 13, 2012 Non-Final Office Action dated Jul. 1, 2019.
U.S. Appl. No. 13/500,853, filed Jul. 13, 2012 Non-Final Office Action dated Oct. 7, 2015.
U.S. Appl. No. 14/283,137, filed May 20, 2014 Advisoary Action dated May 17, 2016.
U.S. Appl. No. 14/283,137, filed May 20, 2014 Final Office Action dated Mar. 3, 2016.

(56) References Cited

OTHER PUBLICATIONS

U.S. Appl. No. 14/283,137, filed May 20, 2014 Non-Final Office Action dated Oct. 22, 2015.
U.S. Appl. No. 14/764,979, filed Jul. 30, 2015 Advisory Action dated May 14, 2019.
U.S. Appl. No. 14/764,979, filed Jul. 30, 2015 Advisory Action dated Nov. 15, 2018.
U.S. Appl. No. 14/764,979, filed Jul. 30, 2015 Final Office Action dated Apr. 4, 2019.
U.S. Appl. No. 14/764,979, filed Jul. 30, 2015 Final Office Action dated Aug. 8, 2018.
U.S. Appl. No. 14/764,979, filed Jul. 30, 2015 Final Office Action dated Nov. 27, 2019.
U.S. Appl. No. 14/764,979, filed Jul. 30, 2015 Non-Final Office Action dated Feb. 7, 2018.
U.S. Appl. No. 14/764,979, filed Jul. 30, 2015 Non-Final Office Action dated Jan. 11, 2019.
U.S. Appl. No. 14/764,979, filed Jul. 30, 2015 Non-Final Office Action dated Jun. 28, 2019.

\* cited by examiner

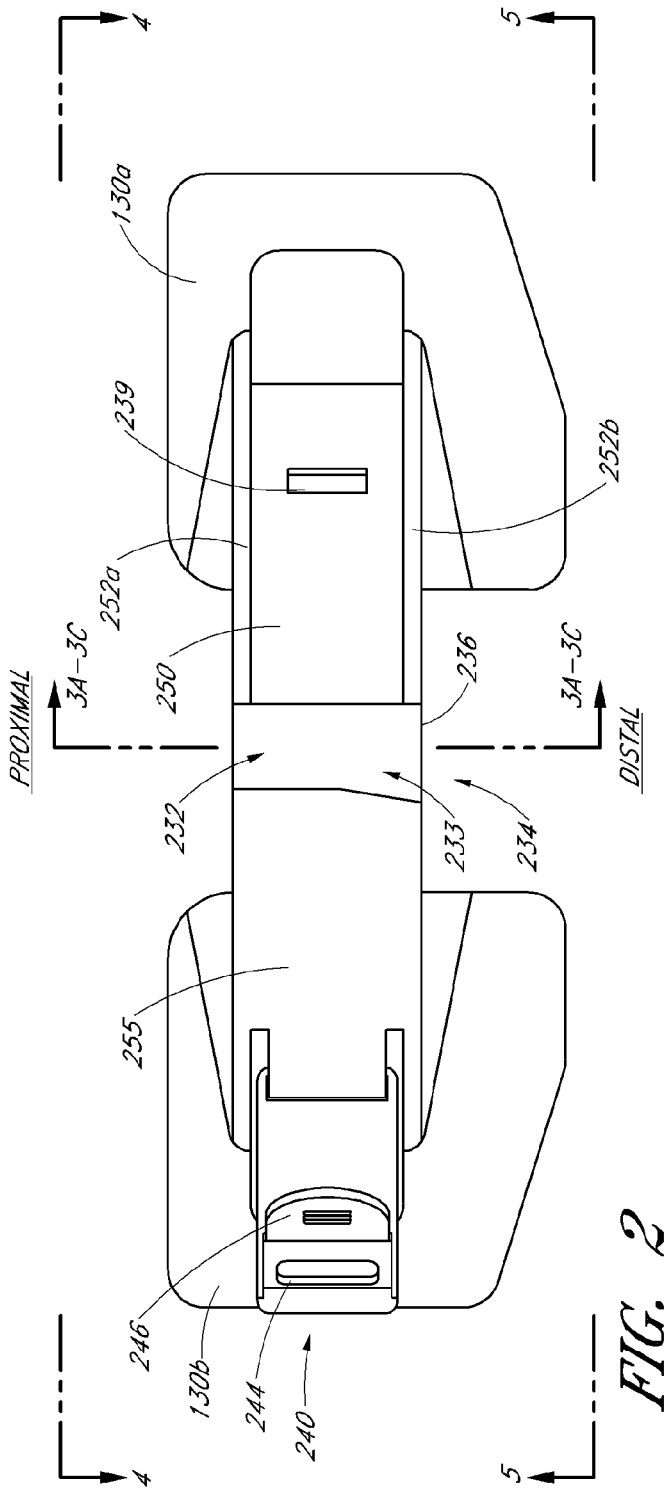
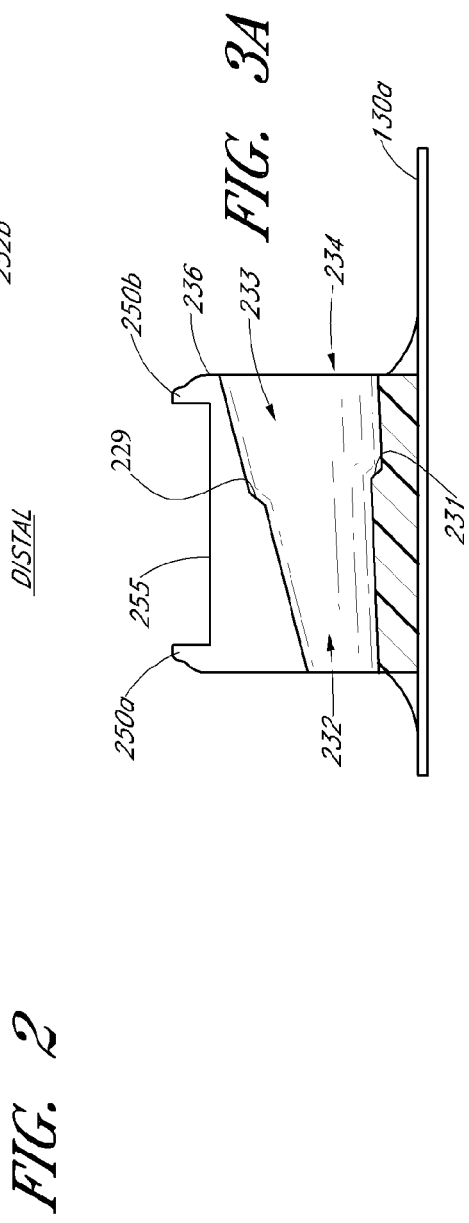

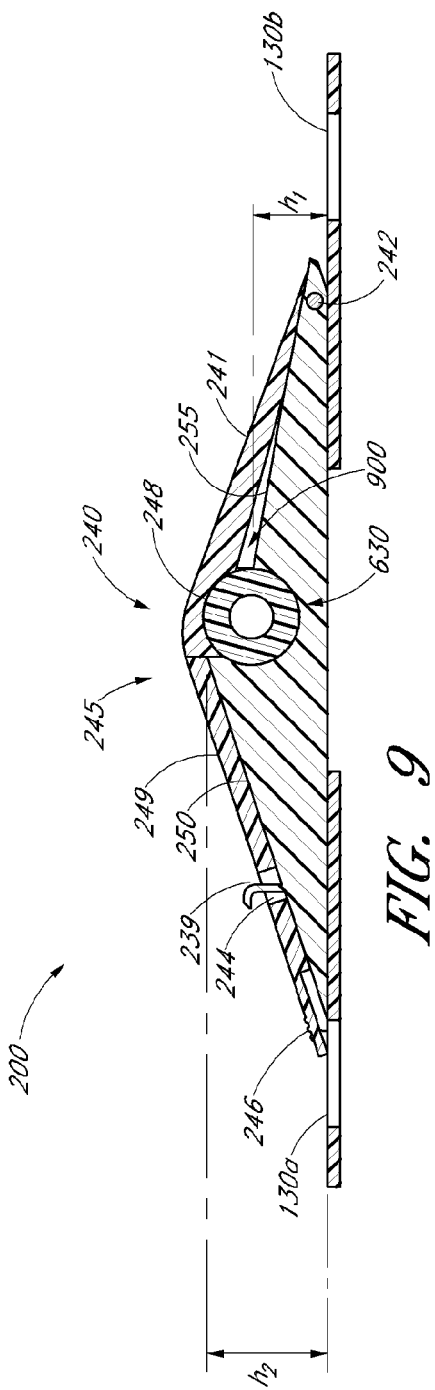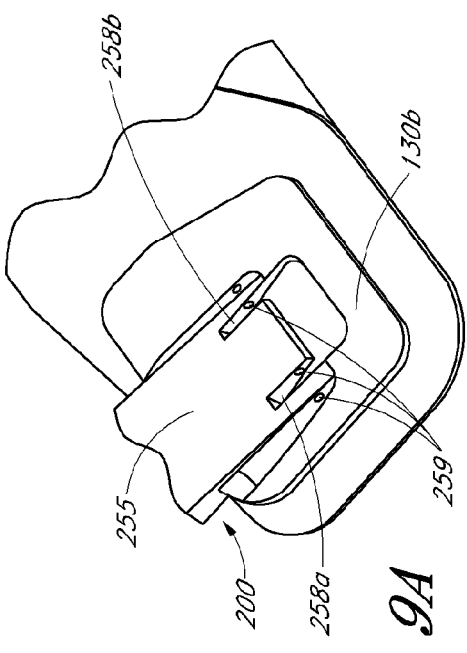

SECUREMENT DEVICE HAVING AN INTEGRAL STRAP AND DRESSING

PRIORITY

This application is a continuation of U.S. patent application Ser. No. 14/764,979, which is a U.S. national stage application of International Patent Application No. PCT/US2014/020207, filed Mar. 4, 2014, claiming the benefit of priority to U.S. Provisional Application No. 61/789,412, filed Mar. 15, 2013, each of which is incorporated by reference in its entirety into this application.

BACKGROUND

Field of the Invention

The present invention relates generally to techniques, systems, and devices for securing a catheter, catheter extension set, and/or other medical article on a patient.

Description of the Related Art

Medical patients are often in need of repetitious administering of fluids or medications, or repetitious draining of fluids. It is very common in the medical industry to utilize medical tubing to provide various liquids or solutions to a patient. For example, medical tubing such as a catheter is often used to introduce fluids and medications directly into the patient or to withdraw fluids from the patient. In many cases, the catheter remains in place for many days. In some instances, a catheter may be attached to a patient for an even lengthier period of time, and may require minimal movement for proper functioning.

It is often advantageous to restrict the movement of the catheter. A moving catheter may cause discomfort to the patient, restrict the administering of fluids or medications or the draining of fluids, cause infection, or become dislodged from the patient unintentionally. In order to keep the catheter or other medical tubing properly positioned for the duration of treatment, the catheter or medical tubing can be stabilized on the patient in a variety of ways. Most commonly, the medical provider may attempt to restrict movement of the catheter by securing the distal end of the catheter, or a portion of a medical device connected to the catheter such as a connector fitting, to the patient using tape. Medical providers commonly place long pieces of tape across the distal end of the catheter, often in a crisscross pattern, to secure the catheter distal end to the patient. This securement is intended to inhibit disconnection between the catheter and the patient or between the catheter and another medical article, such as a drainage tube, as well as to prevent the catheter from catching on other objects, such as on a bed rail.

Stabilizing a catheter with tape upon the patient, however, has certain drawbacks. For example, taped connections often collect contaminants and dirt. This potentially can lead to infection of the patient, particularly at an insertion site where the catheter is inserted into the patient. Taped stabilization typically leaves the insertion site exposed to these contaminants and dirt and other foreign objects that may be harmful to the patient and/or compromise the stabilization of the catheter. Gathering or collecting of contaminants by the tape may exacerbate any problems at the insertion site. Normal protocol therefore requires periodic tape changes in order to inhibit germ growth. Such periodic changes, however, often disrupt any attempts or mechanisms used to shield or protect the insertion site, and may compel detrimental manipulation of the areas around the insertion site. Furthermore, it may be desirable to keep the insertion site of the medical article dry and/or otherwise protected from the external environment in order to reduce infections in and around the insertion site.

BRIEF DESCRIPTION OF DRAWINGS

The above mentioned and other features of the invention will now be described with reference to the drawings of several embodiments of the present stabilization system. The illustrated embodiments of the stabilization system are intended to illustrate, but not to limit the invention. The drawings contain the following figures:

FIG. 2 is a top view of the securement device of FIG. 1.

FIG. 3A is a cross-sectional view of the securement device of FIG. 2 taken along the line 3A-3C according to one embodiment.

FIG. 9 is a cross-sectional view taken along the line 9-9 of the securement device of FIG. 8 with the medical article placed in the closed retainer.

FIG. 9A is a partial top view of the securement device of FIG. 8 with the strap removed.

DETAILED DESCRIPTION OF CERTAIN EMBODIMENTS

Figure 1:
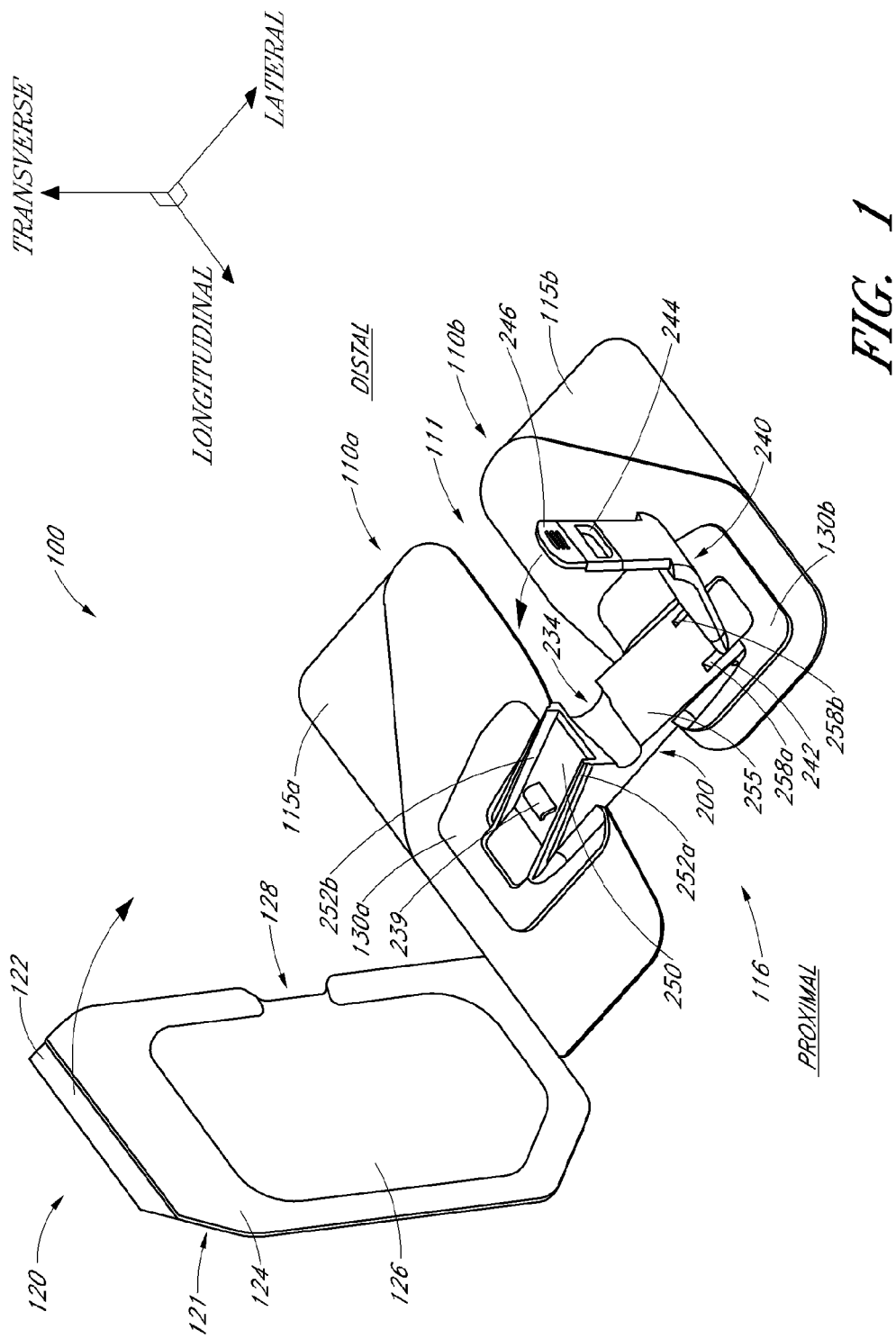
FIG. 1 is a perspective view of an embodiment of a securement device having an integral strap and dressing.

The following description and examples illustrate preferred embodiments of the present securement device disclosed in the context of use with exemplary catheters. More specifically, the embodiments relate to a stabilization device and related techniques that stabilize a medical article in position on a patient. The embodiments of the securement device are illustrated with a catheter in use as part of a peripheral intravenous ("I.V.") line.

It will be understood by those of skill in the art in view of the present disclosure that the securement device described can be used with other types of medical articles, including, but not limited to catheters and catheter hubs of various design, either with or without connectors or extension sets, such as central venous catheters, peripherally inserted central catheters, hemodialysis catheters, Foley catheters, as well as other designs of catheter hubs and catheter adaptors. Other medical articles may include surgical drainage tubes, feeding tubes, chest tubes, nasogastric tubes, rectal drains, external ventricular drains, chest tubes; any other sort of fluid supply or medical lines, connector fittings, and scopes, as well as electrical wires or cables connected to external or implanted electronic devices or sensors. The medical articles can be a single medical article or a combination of medical articles.

The securement device described herein is especially adapted to arrest at least transverse movement of a catheter, as well as to hold medical articles against the patient and protect an area in proximity to an insertion site. The securement device accomplishes this without meaningfully impairing (i.e., substantially occluding) fluid flow through a lumen of the medical article or impairing insertion of the medical article. In some embodiments, retention mechanisms to accomplish this include a channel, a strap that is securable about a medical article, and an integrated dressing. In other embodiments, retention mechanisms to accomplish this include a retention mechanism having a catheter hub, retainer having a channel shaped to receive the hub, and an integrated strap and dressing. The securement device may also prevent movement in a distal and/or proximate direction with respect to the longitudinal axis. In some embodiments, retention mechanisms to accomplish this include a retainer having at least one abutment.

Some embodiments of the securement device releasably engage a catheter hub. An extension set or other medical article can then be attached to the secured catheter hub. This allows the extension set to be disconnected from the securement device, and from the patient, for any of a variety of known purposes, while leaving the catheter secured to the patient. For instance, the medical provider may want to remove the extension set to clean or replace the extension set or to clean an area surrounding where the extension set is located on the patient. The disengagement of the extension set from the securement device, however, can be accomplished without removing an anchor pad, dressing, and/or releasing a retention mechanism. Thus, the medical provider may move the extension set without irritating the skin of the patient or disrupting a catheter (for instance, a cannula) inserted in the skin of the patient.

With reference now to FIG. 1, an embodiment of a securement device 100 includes anchor pads 110a and 100b, base members 130a and 130b, a dressing 120, and a retainer 200. The anchor pad 110 is configured to be secured to a patient's skin. The base members 130a and 103b are attached to an upper surface of the anchor pads 110a and 100b and configured to support the retainer 200. The retainer 200 is configured to engage a medical article, for example a catheter or catheter hub, as will be described in additional detail below.

To assist in the description of the components of embodiments of the securement device, the following coordinate terms are used, consistent with the coordinate axes illustrated in FIG. 1. A "longitudinal axis" is generally parallel to a channel formed by anchor pads 110a and 110b and spanned by the retainer 200. A "lateral axis" is normal to the longitudinal axis and is generally parallel to the plane of the retainer 200. A "transverse axis" extends normal to both the longitudinal and lateral axes. In addition, as used herein, "the longitudinal direction" refers to a direction substantially parallel to the longitudinal axis; "the lateral direction" refers to a direction substantially parallel to the lateral axis; and "the transverse direction" refers to a direction substantially parallel to the transverse axis. The terms "proximal" and "distal" are used in reference to the center of the patient's body, as will be understood by one of skill in the art.

As can be seen in FIG. 1, the anchor pads 110a and 110b are positioned roughly parallel to each other and spaced apart by a gap 111. The gap 111 can form a channel along the longitudinal axis for receiving a medical article such as a catheter. As will be described in greater detail below, the anchor pads 110a and 110b of the embodiment shown in FIG. 1 are shaped for use on a hand of a patient. However, other shapes and configurations of anchor pads 110a and 110b are possible and within the scope of this disclosure. In some embodiments, one anchor pad is used.

The anchor pads 110a and 110b have a lower adhesive surface (not shown) which may adhere to the skin of a patient and an upper layer. The upper layer of the anchor pads 110a and 110b is configured to support at least the retainer 200. In some embodiments, the upper layer is configured to support at least the base members 130a and 130b. In combination, the lower adhesive surface, upper layer, and possibly one or more intermediate layers may comprise a laminate structure. A suitable laminate that comprises a foam or woven material with an adhesive layer is available commercially from Avery Dennison of Painsville, Ohio. The anchor pads 110a and 110b may be configured as a flexible structure configured to conform to the surface of a patient's skin.

The lower adhesive surface or layer may be a medical-grade adhesive and can be either diaphoretic or nondiaphoretic, depending upon the particular application. The lower adhesive surface may have additional types of medical adhesives laminated thereto. In some embodiments, the lower adhesive layer comprises an anti-bacterial or anti-microbial material. For example, the lower adhesive layer may comprise one or more oligodynamic metal salts or oxides, or a combination of salts and oxides. In some embodiments, the lower adhesive layer comprises a silver material, for example a silver salt, colloid, or complex. The adhesive surface may be a solid layer or may be configured as an intermittent layer such as in a pattern of spots or strips. The lower adhesive surface can be applied to the anchor pads 110a and 110b during manufacture, and may be further covered with a release liner as described below. Alternatively, it is possible to apply a double-sided adhesive tape to the upper layer before application.

The upper layer of the anchor pads 110a and 100b may comprise a foam (e.g., closed-cell polyethylene foam) or woven material (e.g., tricot) layer. A surface of the foam or woven material layer constitutes the upper layer of the anchor pads 110a and 110b. In the alternative, the upper layer may comprise an upper paper or other nonwoven cloth layer, and an inner foam layer may be placed between the upper layer and lower adhesive surface.

As shown, the anchor pads 110a and 110b include removable release liners 115a and 115b on a lower surface of the anchor pads 110a and 110b. The removable release liners 115a and 115b may cover the lower adhesive surface before use. The release liners may resist tearing and be divided into a plurality of pieces to assist removal of the release liners and ease attachment of the anchor pads 110a and 110b to a patient's skin. The release liners may be divided into two adjacent pieces. The liners may be made of a paper, plastic, polyester, or similar material. For example, the release liners 115a and 115b may comprise a material made of polycoated, siliconized paper, or another suitable material such as high density polyethylene, polypropylene, polyolefin, or silicon coated paper. As illustrated in FIG. 1, the release liners 115a and 115b include tabs that extend beyond the edge of the anchor pads 110a and 110b to allow a medical provider to easily grip the release liners 115a and 115b and remove them from the anchor pads 110a and 110b. The tabs may be located at any edge of the anchor pads 110a and 110b and may be any suitable size or shape.

With reference now to the dressing 120, it can be seen in FIG. 1 that the dressing 120 is attached to and/or integrated with anchor pad 110a. The dressing 120 is configured to fold, bend, or rotate down over the insertion site area 116 defined by the area in between the anchor pads 110a and 110b and proximal to the retainer 200. A proximal extended portion of the anchor pad 110a can provide an attachment area to attach or integrate the dressing 120 with the anchor pad 110a. Additionally, the extended portion may longitudinally offset the dressing 120 from a location where the retainer 200 is supported by the anchor pad 110a such that when the dressing 120 is folded down over the insertion site, the dressing 120 will not substantially cover or obstruct a catheter hub stabilized by the securement device 100 or the retainer 200 itself.

The dressing 120 and the anchor pad 110a may be formed as an integral, single piece. Alternatively, the dressing 120 and the anchor pad 110a may be formed separately and then attached together. In this case, the dressing 120 and the anchor pad 110a may be attached by any means or mechanism that allows the dressing 120 to fold, bend, or rotate down over the insertion site area. Attachment means include glue or adhesive, a weld of the materials, heat sealing, mechanical fasteners such as staples or eyelets, or other such means of attachment. The anchor pad 110a may be configured in any shape and size that allows attachment or integration of the dressing 120 with the anchor pad 110a. The dressing 120 may be attached to an upper surface of the anchor pad 110a, for example within an outer circumference of the anchor pad 110a. In the illustrated embodiment, the dressing 120 is secured to an edge of the anchor pad 110a that is generally parallel to a longitudinal axis. The dressing 120, however, may be attached to or integrated with the anchor pad 110a such that the dressing 120 is skewed with respect to a longitudinal and/or a lateral axis.

In some embodiments, the anchor pad 110a, the dressing 120, and/or the attachment means described above are configured to allow selective disconnection of the dressing 120 from the anchor pad 110a. For example, when the anchor pad 110a and the dressing 120 are integrally formed, the region in which the dressing pad 120 folds may be scoured such that a medical provider may tear the dressing 120 away from the anchor pad 110a. Of course, other means of removal or release may be employed to allow the dressing 120 to be disconnected from the anchor pad 110a.

A release liner 121 may cover an adhesive surface 124 of the dressing 120 and may also cover an occlusive layer 126 of the dressing 120, as shown in FIG. 1. The adhesive surface 124 is configured to adhere to the skin of a patient and/or to portions of the upper layer of the anchor pads 110a and 110b. The release liner 121 may cover the entire surface of the dressing 120 or may only cover adhesive portions of the dressing 120. As illustrated in FIG. 1, the release liner 121 covers less than the entire surface of the dressing 120 and the edge 122 of the dressing is not covered by the release liner 121. In this way, the uncovered edge 122 can function as a tab, allowing a medical provider to easily grip the release liner and remove it from the dressing 120. In some embodiments, the release liner 121 extends past the edge of the dressing to form a tab. The tab may be located at any edge of the dressing 120, or a tab that projects out from the release liner 121 may be located within an area defined by the edges of the dressing 120. The release liner 121 may include an anti-microbial or anti-bacterial material or coating, and/or have silver particles dispersed throughout. The dressing 120 and release liner 121 may be prepared such that the release liner 121 maintains a covered surface of the occlusive layer 126 in a sterilized state. The release liner 121 may be configured similar to the release liner covering the lower adhesive surface of the anchor pad 110, described above.

In the illustrated embodiment, the adhesive surface 124 is formed in a ring shape on the periphery of the occlusive layer 126. This ring configuration will encircle the insertion site area when the adhesive layer 124 is adhered to the skin of the patient, but will not adhere to the point of insertion. Advantageously, this will reduce the likelihood of aggravating or excoriating the insertion site or skin around the insertion site, and will reduce the likelihood of introducing contaminants and/or liquid near or into the point of insertion. In addition, the adhesive surface 124 will not contact the catheter 610 or catheter hub 630 when the adhesive surface 124 is adhered to the skin. The ring is broken at a notch or indent 128 in the occlusive layer 126 to allow a catheter and/or catheter hub to be covered without being contacted by the adhesive surface 124. Thus, the adhesive surface will not adhere or stick to the catheter and/or the catheter hub. In this way, sticky residues and buildup on the catheter and catheter hub may be reduced or avoided.

The adhesive surface 124 may instead cover all or a majority of the occlusive layer 126. Such configuration will increase the contact area of the adhesive surface 124 with the skin of the patient and with portions of the anchor pads 110a and 110b, and may result in a more secure attachment of the dressing 120 to the patient. The adhesive surface 124 may be configured similar to the lower adhesive surface of the pads 110a and 110b, described above.

The occlusive layer 126 is configured to be waterproof or otherwise impermeable to liquids and in some embodiments also restricts the flow of air. In other embodiments, the occlusive layer 126 may be configured to be breathable, allowing air and/or moisture near an insertion site through to the other side of the occlusive layer 126 and away from the insertion site, while keeping at least external moisture on the other side of the occlusive layer 126 away from the insertion site. In some embodiments, the occlusive layer 126 is impermeable to viruses and bacteria, and may comprise or be coated with an anti-bacterial or anti-microbial material. In some embodiments, the occlusive layer 126 comprises or is coated with a waxy material. In some embodiments, the occlusive layer 126 comprises a film which may or may not be transparent.

Selection of a transparent film or semi-transparent film for use as the occlusive layer 126 may allow a medical provider to see the insertion site and any administered catheter. In this way, potential infections or inflammation may be visualized through the transparent film. In some embodiments, the occlusive layer 126 is absorbent. In some embodiments, the occlusive layer 126 comprises an absorbent acrylic, an alginate, foam, a hydrocolloid, and/or a hydrogel material, and/or may comprise a silver material, for example a silver salt, colloid, or complex. In one embodiment, one or more oligodynamic metal salts or oxides, or a combination of salts and oxides are used in or on the occlusive layer 126 as an antimicrobial agent. In some embodiments, the occlusive layer 126 is configured similar to the upper layer of the anchor pads 110a and 110b.

As described above, the occlusive layer 126 comprises a notch or indentation 128. This notch may reduce stress on the dressing 120 when the dressing is applied over a catheter and/or catheter hub. The dressing 120 may be configured to provide a waterproof seal around an insertion site when applied to the skin of a patient over a catheter and/or catheter hub. In some embodiments, the dressing 120 is still breathable while the waterproof seal is created.

In some embodiments, the dressing 120 comprises a hemostatic dressing. In such embodiments, securing the dressing 120 over an insertion site or other wound may inhibit blood from flowing from the site. For example, the dressing 120 may comprise or be coated with a hemostatic or antihemorrhagic agent such as chitosan or other polysaccharide, a collagen like microfibrillar hemostat, anhydrous aluminum sulfate, potassium alum, titanium dioxide, a gelatin, or a solution of thrombin.

Continuing with FIG. 1, the base members 130a and 130b can have a lower surface secured to the upper surface of the anchor pads 110a and 110b and an upper surface secured to at least a portion of the lower surface of the retainer 200. Although the base members 130a and 130b are shown as having a roughly rectangular shape with rounded ends, the base members 130a and 130b may be shaped in any of a multitude of ways. The base members 130a and 130b can be formed with the same or different materials as the retainer 200. In one embodiment, the base members 130a and 130b and the retainer 200 comprise a single, integral piece. The base members 130a and 130b, anchor pads 110a and 110b, and retainer 200 may be secured together by any means or mechanism including glue or adhesive, a weld of the materials, heat sealing, mechanical fasteners such as staples or eyelets, or other such means of attachment. In some embodiments, the base members 130a and 130b are semi-rigid or flexible. In this way, the base members 130a and 130b can provide a transition between the relatively pliable anchor pads 110a and 110b and the relatively rigid retainer 200. For example, the base members 130a and 130b may help secure the retainer 200 to the anchor pads 110a and 110b and stabilize the retainer 200 so as to better withstand twisting about the lateral axis.

With reference now to the retainer 200, it can be seen in FIG. 1 that the retainer 200 comprises an open channel 234, a strap 240, and two angled supports 250 and 255. The retainer 200 is attached to and supported by the base members 130a and 130b and is configured such that the retainer 200 does not rock or otherwise pivot on the base members 130a and 130b. In some embodiments, the retainer 200 is permanently adhered or affixed to the base members 130a and 130b.

The open channel 234 has a curvilinear shape configured to accept at least a portion of a medical article. In the illustrated embodiment, the open channel 234 is configured to accept a catheter hub and thus the shape of the channel 234 approximates at least a portion of the catheter hub. The channel 234 is shown as having an approximately semiconical shape, but may be formed as having a different shape. In the illustrated embodiment, the width of the channel 234 in the lateral direction varies in width such that a portion of the channel tapers in a direction from distal to proximal, but the channel 234 may be a consistent width or tapered along the entire channel. As will be described below, the channel 234 may be configured to accept various medical articles.

A strap 240 is attached to the first angled support 255. The strap 240 is configured to close over the open channel 234 and onto the second angled support 250 to form an enclosed area. When at least a portion of a medical article is placed inside the channel 234, the strap 240 can be moved over the medical article to retain or stabilize the medical article within the retainer 200 by, for example, applying a downward force onto the medical article and thus maintaining at least a portion of the medical article on a surface of the channel 234. The strap 240 may be integral to the first angled support 255, or may be attached thereto. In one embodiment, the strap 240 is integral to the first angled support 255 and attached by a living hinge. In another embodiment, the strap 240 is formed separate from the first angled support 255 and attached thereto, for example by sonic welding. A multitude of attachment means may be used to attach the strap 240 to the first angled support 255 such that the strap 240 may be closed over the channel 234 and onto the second angled support 250.

As illustrated in FIG. 1, the strap 240 is attached to the first angled support 255 by a pin 242 that passes through the first angled support 255 and the strap 240. As such, the strap 240 can rotate about the pin 242 to cover and uncover channel 234. The first angled support 255 includes grooves 258a and 258b for receiving a portion of the strap 240 when the strap 240 is in a closed position.

In one embodiment, the strap 240 comprises an elastomeric material. In this embodiment, the strap 240 may be stretched or deformed slightly when closing about a medical article placed in the channel 234. That is to say, the strap 240 may conform to the outer surface of a medical article placed within the channel 234 thus increasing the contact area between the medical article and the strap 240. Such elastic deformation may increase the stability with which the medical article is secured within the channel 234. In addition, the elastomeric material may have an increased frictional coefficient with the medical article as compared to certain other materials like hard plastics. In some embodiments, the strap 240 may also have ribs or other protrusions formed on an inside surface thereof. In this way, the ribs can further increase the frictional coefficient with the medical article to further secure the medical article within the retainer 200.

In the illustrated embodiment, the strap 240 is formed with an opening 244 therethrough. The opening 244 is configured to accept a retention mechanism 239. The retention mechanism 239 is disposed on the second angled support 250 in the illustrated embodiment. The second angled support 250 holds the retention mechanism 239 in a position such that it can engage with the strap 240. The second angled support 250 may also serve to support, strengthen, or stabilize a portion of the channel 234. In some embodiments, the second angled support 250 is omitted. In this case, the retention mechanism 239 may be disposed on an outer surface of the channel 234 or on the base member 130a.

In FIG. 1, a first securement mechanism, e.g., the retention mechanism 239, is illustrated as being a protrusion disposed on the second angled support 250 that can be inserted through the opening 244 to retain the strap 240 in a closed position over the channel 234. The retention mechanism 239 may comprise a lip to overhang a portion of the strap 240 after the retention mechanism 239 has been inserted through the opening 244. Other securing means may be used in place of the illustrated retention mechanism 239. For example, the strap 240 may be secured about a medical article by a snap, adhesive, hook and loop fasteners, or other securing means.

With continued reference to FIG. 1, a tab 246 extends away from the portion of the strap 240 and has the opening 244. The tab 246 may be formed of the same or different material as the strap 240. The tab 246 may include ridges, bumps, or other raised features to distinguish the tab 246 from the strap 240. The tab 246 may allow a medical provider to easily grip the strap 240 and to engage and/or disengage the strap 240 from the retention mechanism 239. In some embodiments, the tab 246 has a thickness less than the strap 240 and/or may be configured to move about the end of the strap 240. In some embodiments, the tab 246 is omitted.

In the illustrated embodiment, the second angled support 250 comprises a second securement mechanism, e.g., protrusions 252a and 252b along each edge of the second angled support 250. As shown, the protrusions 252a and 252b are integrally formed with the second angled support 250 and run along the entire length of the second angled support 250 forming a channel that can receive a portion of the strap 240. The protrusions 252a and 252b can limit movement of the strap in the longitudinal direction when the strap 240 is secured over the channel and onto the second angled support 250. In some embodiments, the protrusions 252a and 252b are formed separately and are attached to the second angled support 250. In some embodiments, the protrusions 252a and 252b do not cover the entire length of the second angled support 250. In some embodiments, the second angled support 250 includes a single protrusion along one edge of the second angled support 250.

The retainer 200 may be constructed as a single piece or from a plurality of different pieces. For example, the entire retainer 200 may be formed by injection molding, or the channel 234 and the angled supports 250 and 255 may be formed separately and thereafter joined together. The retainer 200 or portions thereof may be rigid or flexible. Suitable materials may include, for example, but without limitation, plastics, polymers or composites such as polypropylene, polyethylene, polycarbonate, polyvinylchloride, acrylonitrile butadiene styrene, nylon, olefin, acrylic, polyester, as well as moldable silicon, thermoplastic urethane, thermoplastic elastomers, thermoset plastics and the like. In one embodiment, the retainer 200 is formed by injection molding using a polyethylene or a polypropylene material or nylon. However, other materials can be utilized.

FIG. 2 is a top view of the retainer 200 shown in FIG. 1. From above, the geometry of the channel 234 of one embodiment of the retainer 200 can be appreciated. The channel 234 may comprise a distal portion 233 and a proximal portion 232. As shown, the width of the distal portion 233 is greater than the width of the proximal portion 232. In this way, the channel 234 can be sized and shaped such that a complementary shaped medical article can fit snuggly within the channel 234. In other words, the particular dimensions of the channel 234 can be adjusted such that the contact area between the medical article and the channel 234 is maximized.

FIG. 3A is a cross-sectional view of the retainer 200 in FIG. 2 taken along the line 3A-3C. This cross-sectional view further exemplifies the geometry of the channel 234 of one embodiment of the retainer 200. As shown, the interior of the channel 234 includes a lower abutment surface 231 and an upper abutment surface 229. The lower and upper abutment surfaces 231 and 229 can prevent a suitably shaped medical article from moving in at least a proximal direction. The channel 234 also includes an upper abutment 236 on the exterior of the channel. The upper exterior abutment 236 can contact a portion of a medical article placed within the channel 234. For example, the upper exterior abutment 236 can contact a proximal surface of a catheter fitting attached to a catheter hub positioned within the channel 234, as will be described in greater detail below, so as to prevent movement of the catheter fitting in the proximal direction. Similarly, the upper exterior abutment 236 can contact a surface of a catheter hub positioned within the channel 234. For example, the upper exterior abutment 236 can contact a proximal surface of a male luer-lock portion of a catheter hub positioned within the channel 234.

Figure 3B:
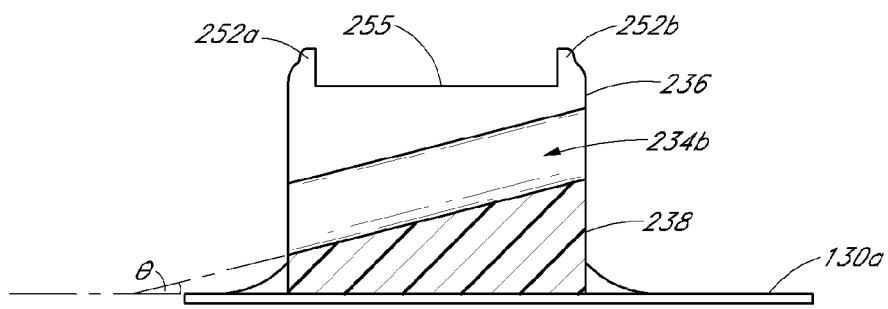
FIG. 3B is a cross-sectional view of the securement device of FIG. 2 taken along the line 3A-3C according to another embodiment.

FIG. 3B is a cross-sectional view of a retainer 200 in FIG. 2 taken along the line 3A-3C according to another embodiment. As illustrated, the channel 234b in this embodiment does not include interior abutment surfaces. Furthermore, the width of the channel 234b is uniform. The channel 234b also includes an upper exterior abutment 236 and a lower exterior abutment 238. The upper exterior abutment 236 and/or lower exterior abutment 238 can contact a portion of a medical article placed within the channel 234b as described above. The inclination angle θ of the channel 234b with respect to the transverse direction may be any suitable angle. In some embodiments the inclination angle θ is between about 5 and about 10 degrees, for example, about 7 degrees, relative to the patient's skin.

Figure 3C:
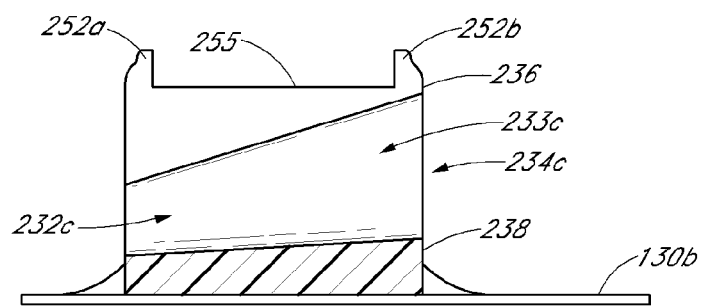
FIG. 3C is a cross-sectional view of the securement device of FIG. 2 taken along the line 3A-3C according to another embodiment.

FIG. 3C is a cross-sectional view of a retainer 200 in FIG. 2 taken along the line 3A-3C according to another embodiment. As shown, in this embodiment, the width of the channel 234c is not uniform. Rather, the width of the distal portion 233c of the channel 234c is greater than the width of the proximal portion 232c of the channel 234c. In this way, the channel 234c can be shaped to receive, for example, a conically shaped medical article. Such a conically shaped medical article, positioned within the channel 234c, can abut the surface of the channel 234c and thus can be prevented from moving in the proximal direction.

Figure 4:
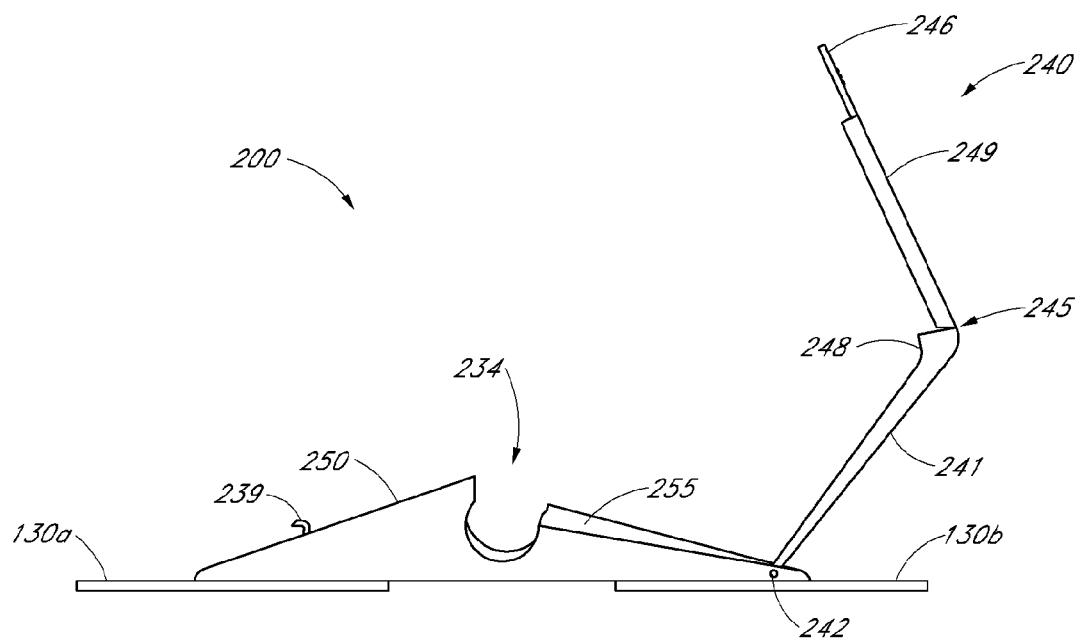
FIG. 4 is a front view taken from the proximal end of the securement device of FIG. 1.

FIG. 4 is a front view taken from the proximal end of a retainer 200 of FIG. 1 according to one embodiment. From this view, the shape of the channel 234 can be further appreciated. As shown, the channel 234 is shaped roughly as an inclined tapered cylindrical section. FIG. 4 illustrates that the channel 234 is slightly angled such that a distal portion of the channel slopes downward toward a proximal portion of the channel. In this way, a medical article placed within the channel 234 can be retained within the channel 234 and supported at a desired insertion angle with respect to the transverse axis. The channel 234 also narrows in width from the distal portion towards the proximal portion. As such, the channel 234 is shaped to receive a roughly conically shaped medical article that tapers in the proximal direction.

FIG. 4 also illustrates that the first angled support member 255 slopes downward from a distal portion of the first angled support member 255 towards a proximal portion of the first angled support member 255. In some embodiments, the angle of inclination of the first angled support 255 in the longitudinal direction is roughly the same as a roughly conically shaped medical article, tapered in the proximal direction. That is to say, the first angled support member 255 can be shaped such that a complementary shaped medical article can fit snuggly against the first angled support member 255. This configuration can allow the strap 240 to contact a greater area on the upper surface of the first angled support member 255 when the strap 240 is closed over the channel 234.

Continuing with FIG. 4, the strap 240 comprises a first strap section 241 and a second strap section 249. When the strap 240 is positioned over the channel 234, the first strap section 241 can contact the first angled support member 255 and a medical article positioned within the channel 234 while the second strap section 249 can contact the second angled support member 250 and engage the retention mechanism 239. The first strap section 241 and second strap sections 249 can comprise the same material as each other or be formed of different materials. For example, the first strap section 241 can comprise a rigid material while the second strap section 249 can comprise an elastomeric material. The first strap section 241 and second strap sections 249 can be formed as one integral strap joined by a hinge 245 (for example, a living hinge) or formed separately and coupled together.

As shown in FIG. 4, the first strap section 241 has a lower surface shaped to receive a portion of a medical article. The first strap section 241 generally increases in thickness in a direction away from the first angled support member 255 and includes an indentation 248. The second strap section 249 has a thickness less than the thickness of the first strap section 241. However, the relative thicknesses of the first and second strap sections 241 and 249 can be the same and the second strap section 249 can have thickness greater than the thickness of the first strap section 241. The indentation 248 can be shaped to receive at least a portion of an upper surface of a medical article, for example, the upper surfaces of a catheter hub. In one embodiment the indentation 248 is curvilinearly shaped. In this way, the strap 240 can be sized and shaped such that a complementary shaped medical article can fit snuggly against the strap 240. In other words, the particular dimensions of the strap 240 can be adjusted such that the contact area between the medical article and the strap 240 is maximized.

Figure 5:
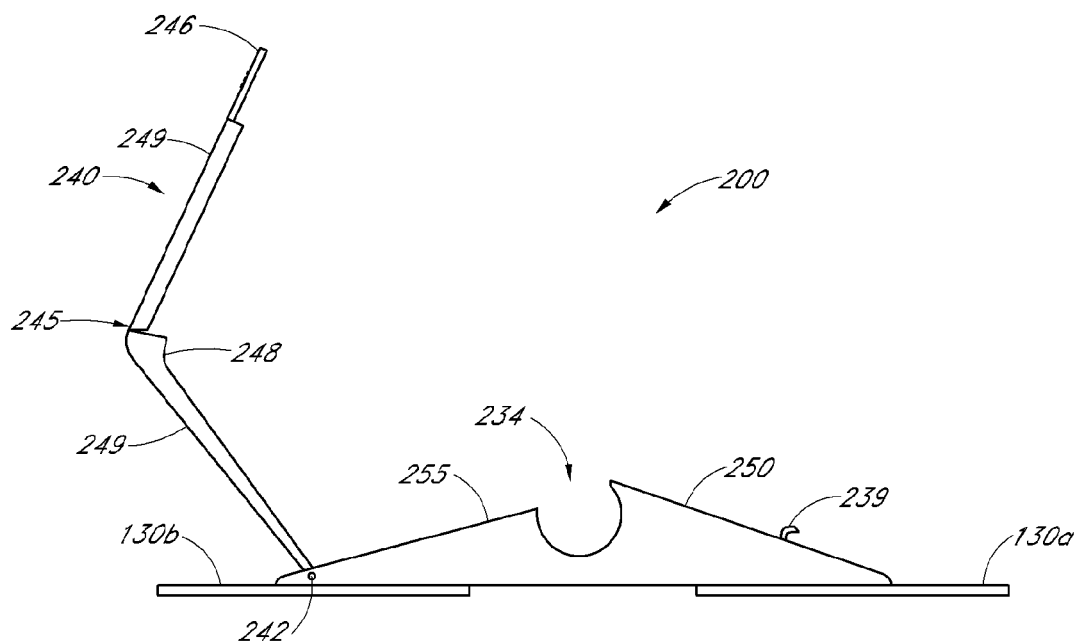
FIG. 5 is a rear view taken from the distal end of the securement device of FIG. 1.

FIG. 5 is a rear view taken from the distal end of the retainer 200 of FIG. 4. From this view, one can further appreciate the geometry of the channel 434 according to the illustrated embodiment. As shown, the channel 234 is crescent shaped and greater than semi-circular when viewed from the distal end of the securement device 100. As such, the channel 234 can receive a medical article inserted from both the transverse and/or longitudinal directions while at the same time the contact area between the channel 234 and the exterior surface of the medical article placed therein can be maximized. In some embodiments, the channel 424 does not have generally rounded sides. For example, the sides of the channel 234 may be angled in relation to themselves or in relation to each other to accommodate a differently shaped medical article.

Figure 6:
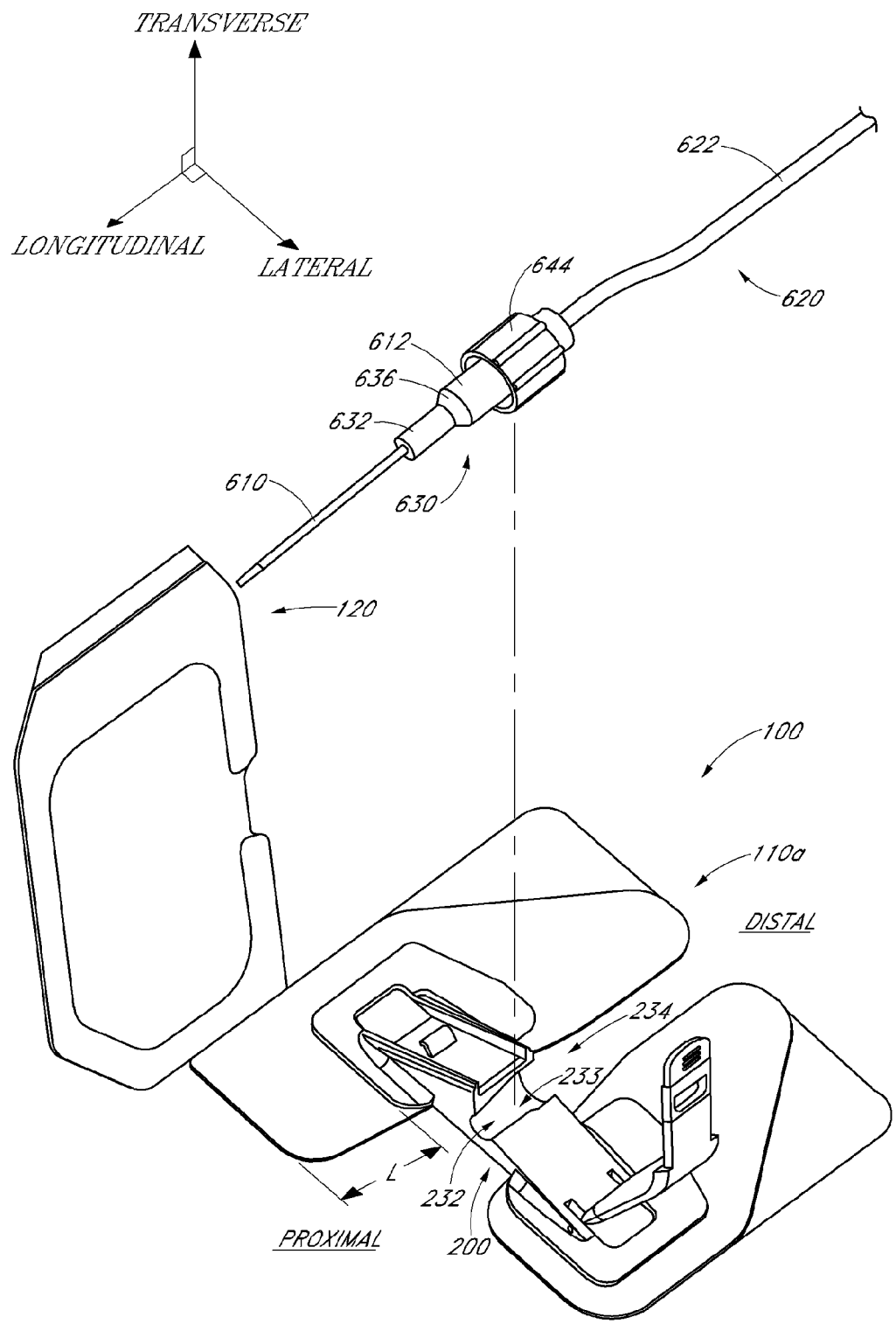
FIG. 6 is another perspective view of the securement device of FIG. 1 and shows a medical article positioned above the device.

FIG. 6 illustrates the securement device 100 in FIG. 1 with a medical article positioned above. As shown, a catheter 610 is attached to a catheter hub 630. In some embodiments, the catheter 610 or a portion thereof comprises or is coated with an antimicrobial agent and/or an antibacterial agent. The antimicrobial agent may comprise a silver material, for example a silver salt, colloid, or complex. In one embodiment, one or more oligodynamic metal salts, oxides, or combination of salts and oxides are used.

FIG. 6 shows that anchor pad 110a can extend a length L in the proximal direction away from the retainer 200. This length L can serve as attachment surface for the dressing 120. In this way, the dressing 120 can be positioned in an open position, away from the insertion site to allow easy access to the insertion site for a medical article. After the medical article is inserted into the patient, the dressing 120 can be folded over the length L to further protect the insertion area and secure the medical article to the patient.

Catheter hubs are generally known to those skilled in the art. The catheter hub 630 shown in FIG. 6 has a proximal body 632, a conical section 636, and a distal body 612. However, different catheter hubs may include more or less bodily sections of various different shapes and sizes, all of which may be used with the retainer 200 or other embodiments of the retainers described herein. In one embodiment, the catheter hub 630 comprises an integral one-way valve. The catheter hub 630 is connected to an extension set 620. The extension set 620 illustrated in FIG. 6 includes a spin nut 644 connected to a tube 622. The channel 234 is shaped to receive the catheter hub 630. For example, the proximal portion of the channel 232 is shaped to receive the proximal body 632 and the distal portion of the channel 233 is shaped to receive the distal body 612.

Figure 7:
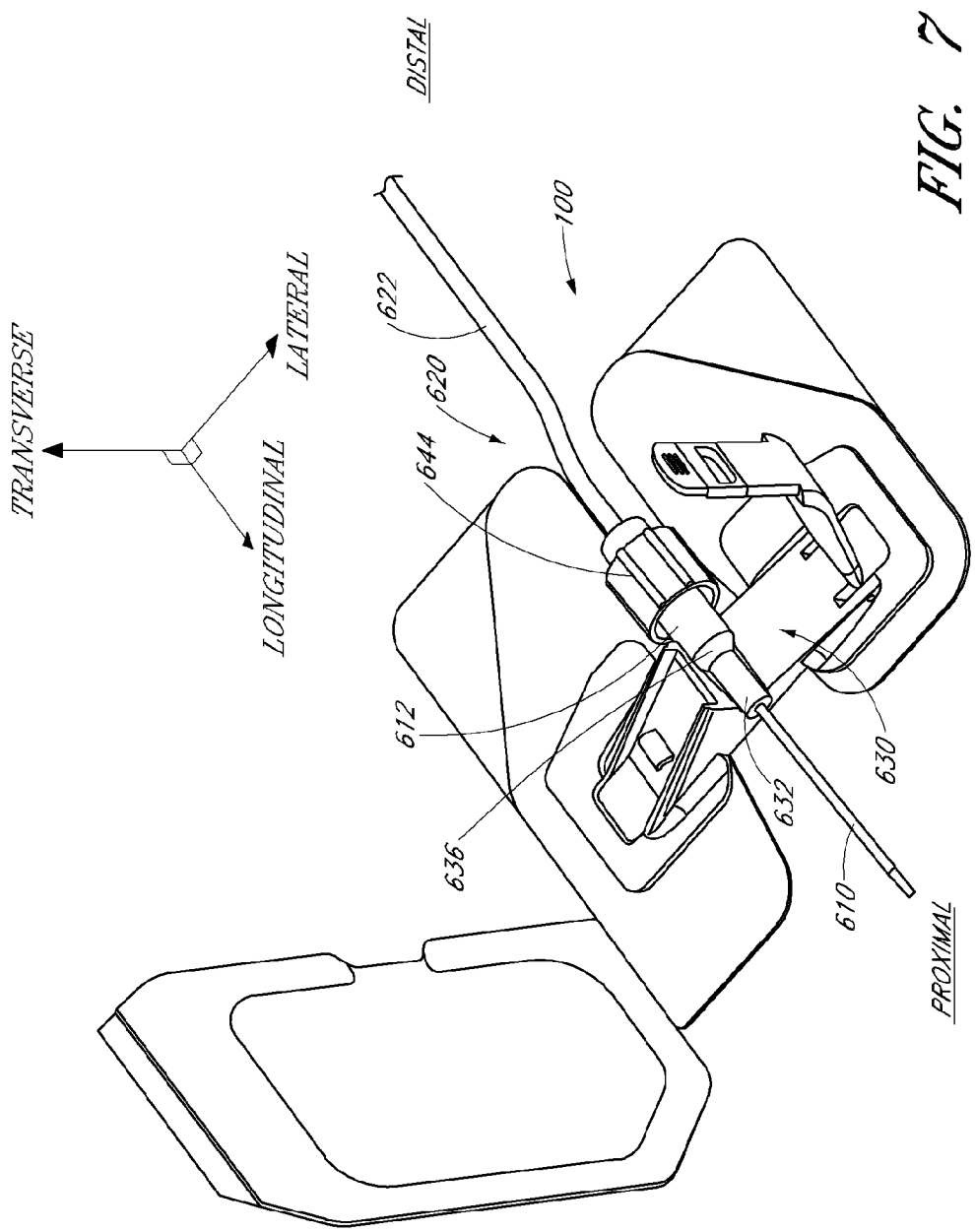
FIG. 7 is another perspective view of the securement device of FIG. 1 and shows a medical article placed in the open retainer.

Turning to FIG. 7, the catheter hub 630 may be placed within the open retainer 200 from above. With brief reference to FIG. 3B, one can appreciate that the conical section 636 may contact the lower and upper abutment surfaces 231 and 229 within the channel 234. As such, the catheter hub 630 is prevented from moving in a proximal direction by at least one abutment surface.

Figure 8:
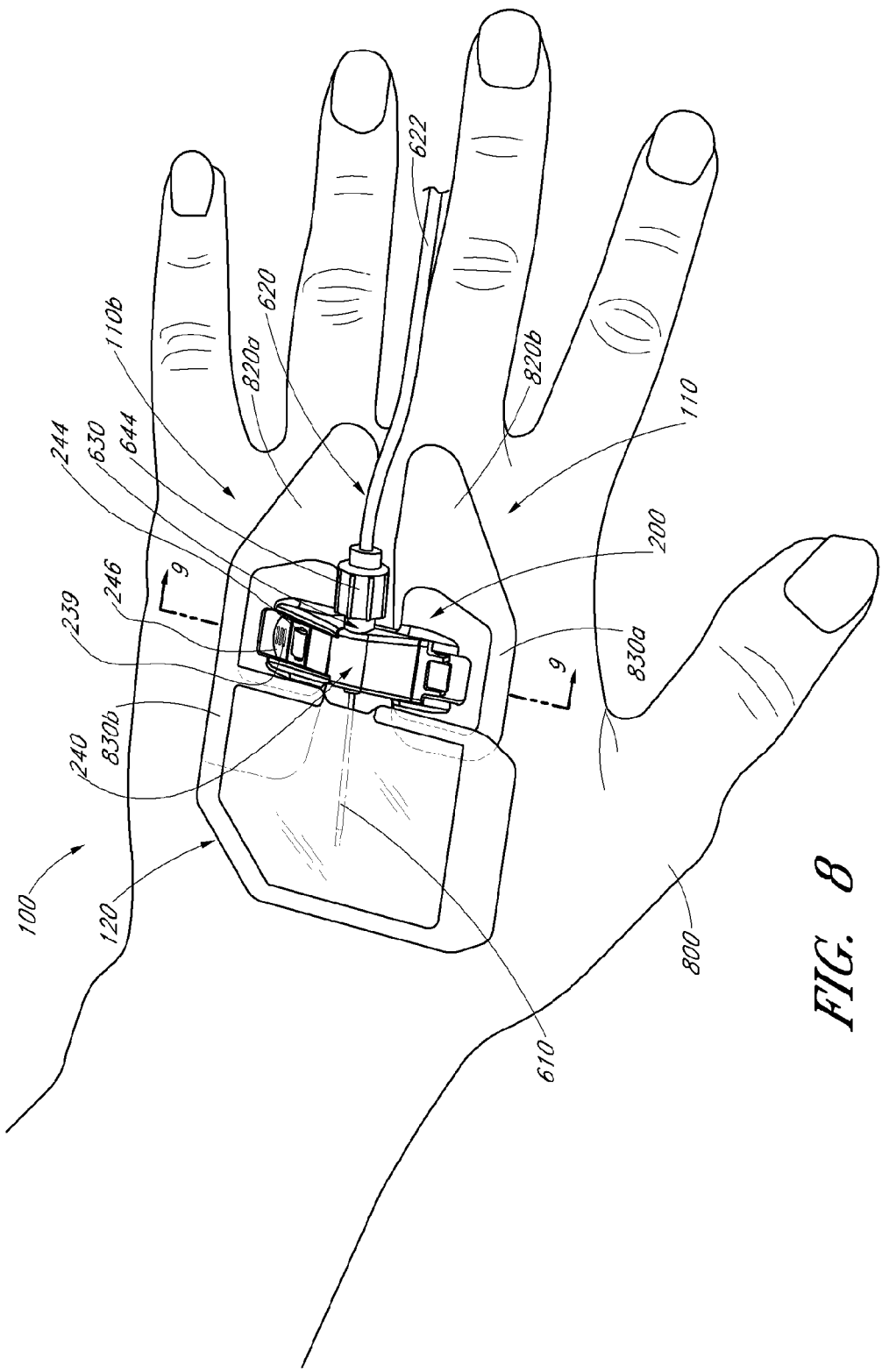
FIG. 8 is a top view of the securement device of FIG. 1 secured to a patient with the dressing folded against the patient with the retainer in the closed position.

Moving on to FIG. 8, the securement device 100 is illustrated as secured to a hand 830 of a patient. Those of skill in the art, however, will recognize that the securement device 100 may instead be secured to other portions of a patient's body. Those of skill in the art will understand that the relative positioning of various elements of the securement device 100 thus may be altered without compromising the advantages provided by the securement device 100. In some embodiments, the securement device 100 is configured as a mirror image of the device shown in FIG. 8.

Continuing with FIG. 8, the anchor pads 110a and 110b comprise distal triangular sections 820a and 820b with rounded corners and proximal rectangular sections 830a and 830b with rounded corners. The proximal rectangular sections 830a and 830b support the base members 130a and 130b and retainer 200 while the distal triangular sections 820a and 820b further attach the securement device 100 to the left hand 800. For example, the lower surface of the distal triangular sections 820a and 820b can adhere to an area proximal to the knuckles of the hand. However, other shapes and configurations of the anchor pads 110a and 110b are possible and within the scope of this description. For example, the anchor pads 110a and 110b, may be larger or smaller, and may be shaped for placement on a different area of the patient's body. In short, the anchor pads 110a and 110b may be any size or shape that allows attachment of the anchor pads 110a and 110b to a patient's skin and that is configured to support at least the retainer 200.

In the illustrated embodiment, the strap 240 is configured to retain the catheter hub 630. Thus, the strap 240 is sized and shaped such that it can be placed over the portion of the catheter hub 630 that is exposed after the catheter hub 630 has been placed in the channel. When the strap 240 is formed of an elastomeric material, as described above, the strap 240 may conform to the shape of the catheter hub 630 or other retained medical article when pulled over the medical article or portion thereof. In the illustrated embodiment, the strap 240 does not secure the spin nut 644. That is to say, when the strap 240 is closed over the catheter hub 630, the spin nut 644 can be rotated to release the extension set 620 from the catheter hub 630 while the catheter hub 630 remains secured to the patient.

The catheter 610 can be inserted into the hand 800 and the catheter hub 630 can be connected to the extension set 620 by using the spin nut 644 before or after the catheter hub 630 is placed in the channel of the retainer 200. The anchor pads 110a and 110b may have already been adhered to the hand 800, or the anchor pads 110a and 110b may thereafter be adhered to the hand 800. During this time, the dressing 120 is held away from the catheter 610 and the insertion site. The positioning of the dressing 120 may be maintained by a medical provider, or the dressing 120 or the area of attachment of the dressing 120 to anchor pad 110b may be configured so as to bias the dressing 120 in this position.

The strap 240 is then pulled over the catheter hub 630 until the opening 244 engages the retention mechanism 239. The retention mechanism 239 will maintain the strap 240 in a closed position over the catheter hub 630. At this time, the release liner 122 of the dressing is removed to expose the adhesive surface 124. The dressing 120 is folded down over the insertion site and adhered to the skin of the patient, as shown in FIG. 8. Of course, the dressing 120 may be adhered to the patient before the strap 240 is closed over catheter hub 630 and secured by the retention mechanism 239. To remove the catheter hub 630 from the retainer 200, the medical provider may use the tab 246 to release the strap 240.

In this way, the catheter 610, catheter hub 630, and extension set 620 may be stabilized by the securement device 100. In addition, the insertion site of the catheter will be protected and preserved in a sanitary fashion while the catheter is administered. The medical provider can ensure such protection at the time of stabilization of the catheter, and need not leave the inserted catheter unattended to seek a form of protective covering for the insertion site.

Turning to FIG. 9, a cross-sectional view taken along the line 9-9 of the retainer 200 of FIG. 8 is illustrated. As shown, the strap 240 is closed over the channel and secured by retention mechanism 239. In the closed position, the lower surface of the strap 240 contacts at least a portion of first angled support 255, at least a portion of the catheter hub 630 positioned in the channel of the retainer 200, and at least a portion of the second angled support 255. The indentation 248 in the first strap section 241 can be shaped to accept the upper surface of a catheter hub 630 placed within the channel. The first strap section 241 contacts less than the total surface area of the first angled support 255 such that a gap 900 exists between the first strap section 241 and the first angled support 255. The gap 900 may ensure that the entire underside of the strap 240 above the catheter hub 630 contacts the catheter hub 630. However, the gap 900 is not required, and the strap 240 and/or the first angled support 255 can be shaped such that no gap 900 is present when the strap 240 is closed over a medical article placed within the retainer 200.

The first strap section 241 can also contact a portion of the second angled support 255. FIG. 9 also shows the relative heights $h_1$ and $h_2$ of the first and second angled supports 255 and 250 above the top surfaces of the base members 130a and 130b. As shown, the height of the first angled support $h_1$ is greater than the height of the second angled support $h_2$.

FIG. 9A shows a partial top view of the securement device of FIG. 8 with the strap removed. As shown, the second angled support 255 comprises two channels 258a and 258b. The channels 258a and 258b can serve as receiving spaces for at least a portion of the strap 240. The strap can be shaped such that a portion of the strap can fit within the channels 258a and 258b. The strap can also include a bore through the end of the strap to be attached to the second angled support 255. The bore can be configured to receive a pin. The second angled support 255 can also include bores 259 for receiving a pin therethrough. In other words, a pin can pass through the second angled support 255 and the strap in order to movably attach the strap to the retainer.

Figure 10:
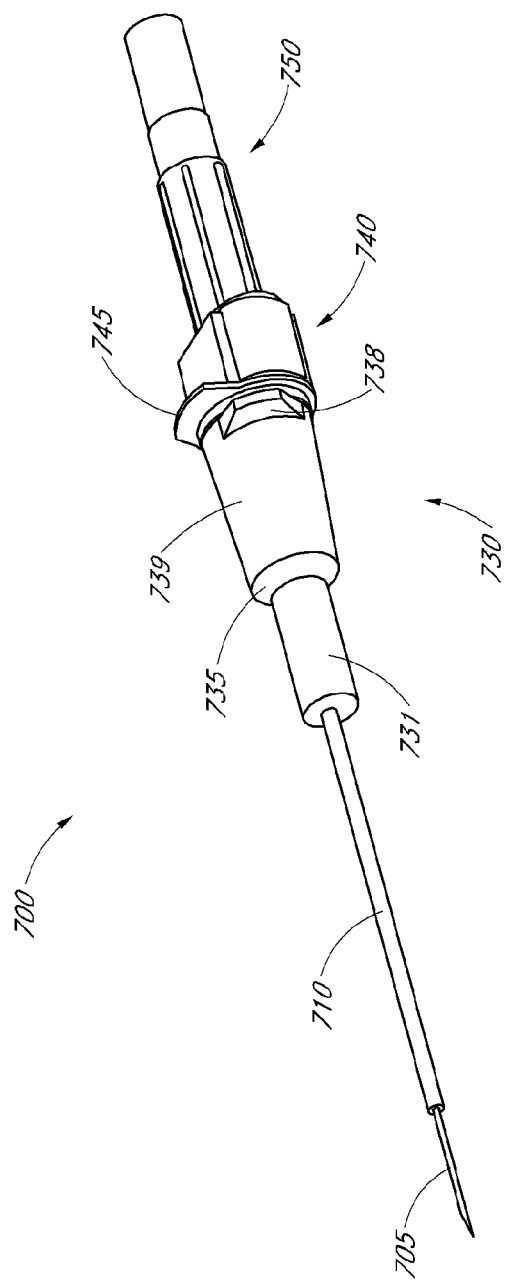
FIG. 10 is a perspective view of a medical article.

FIG. 10 illustrates a catheter assembly 700 that can be used with some embodiments of the securement device described herein. In some embodiments, the securement device is configured to retain the catheter assembly 700. The catheter assembly 700 can be an ADVANTIV® safety I.V. catheter available from Smiths Medical (Dublin, Ohio) or a similar catheter. As shown, the catheter assembly 700 comprises an introducer needle 705, a catheter 710, a catheter hub 730, a tip protector 740, and a flash chamber assembly 750. The catheter hub 730 has a proximal body 731 and a distal body 739. The distal body 739 has an abutment surface 735 and a male luer-lock connector 738. The abutment surface 735 can contact at least a portion of a retainer to prevent the catheter hub 730 from moving in at least a proximal direction. The male luer-lock connector 738 can be used to connect the catheter hub 730 to a catheter extension set.

Figure 11:
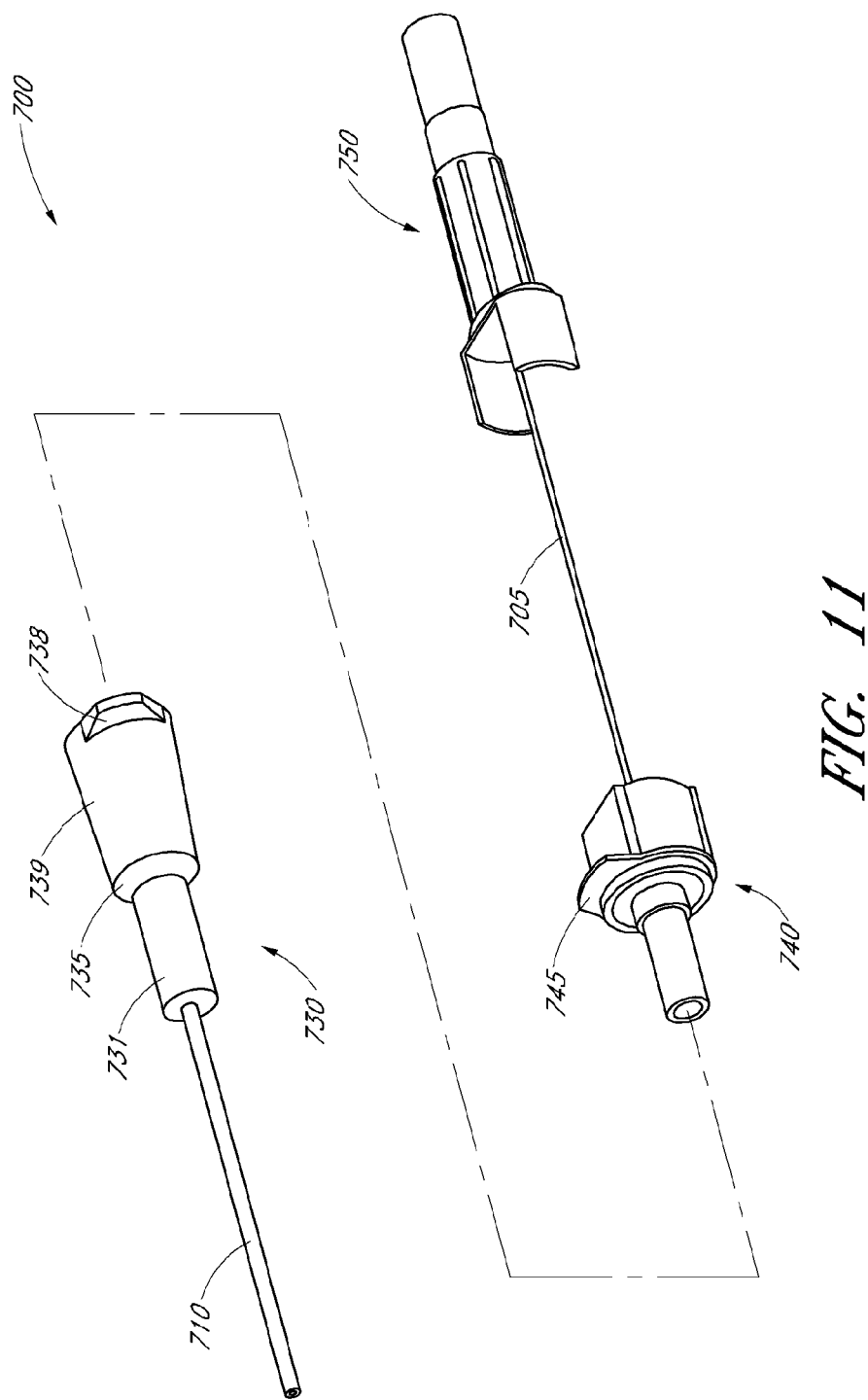
FIG. 11 is an exploded view of the medical article of FIG. 10.

FIG. 11 illustrates an exploded view of the catheter assembly 700 of FIG. 10. As shown, the tip protector 740 encloses the sharp proximal end of the introducer needle 705 and includes a tab 745. A medical provider may apply a force to a distal surface of the tab 745 while pulling on the flash chamber assembly 750 to remove the flash chamber assembly 750, introducer needle 705, and tip protector 740 from the catheter hub 730. When the introducer needle 705 is moved distally, away from the catheter hub 730, the sharp proximal end of the introducer needle 705 engages with the tip protector 740 such that the tip protector 740 encloses the proximal tip portion of the introducer needle 705. In this way, the sharp tip of the introducer needle 705 is shielded, for example, to reduce the likelihood of accidental needle pricks.

Figure 14:
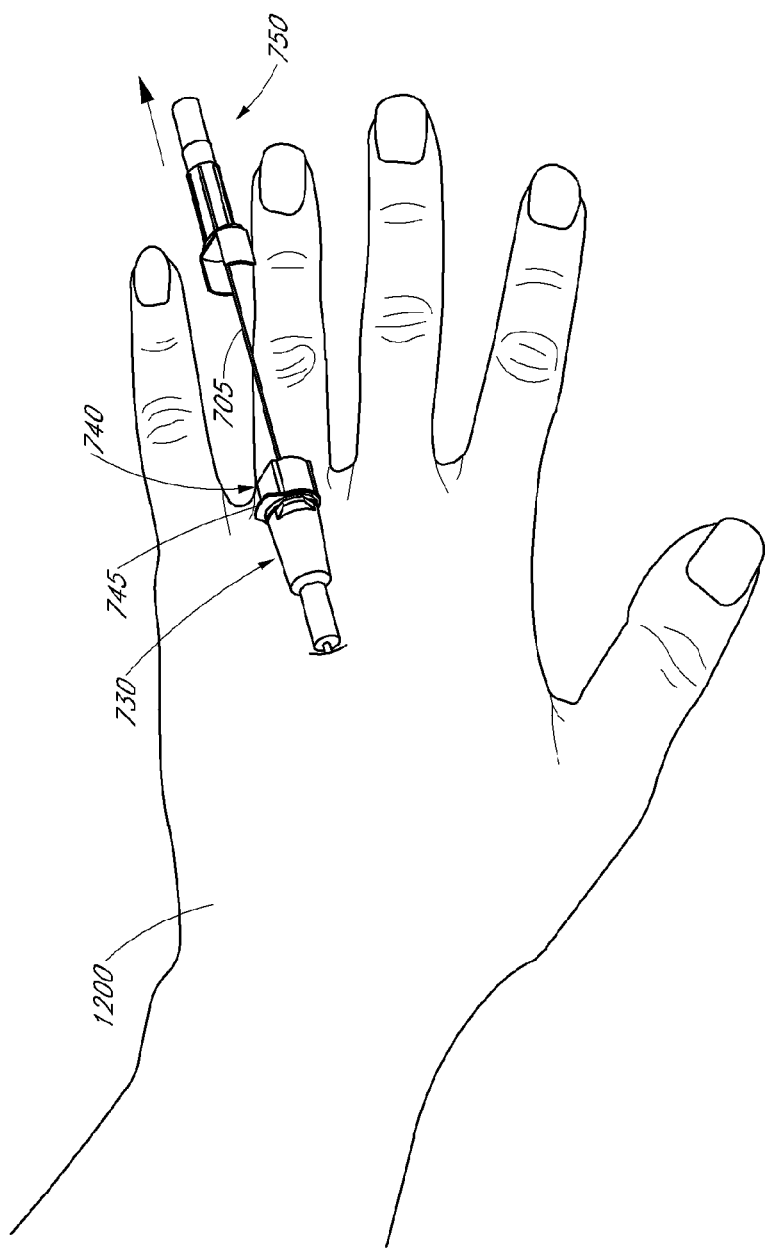
FIG. 14 is another perspective view of the medical article of FIG. 10 being used with a patient.
Figure 15:
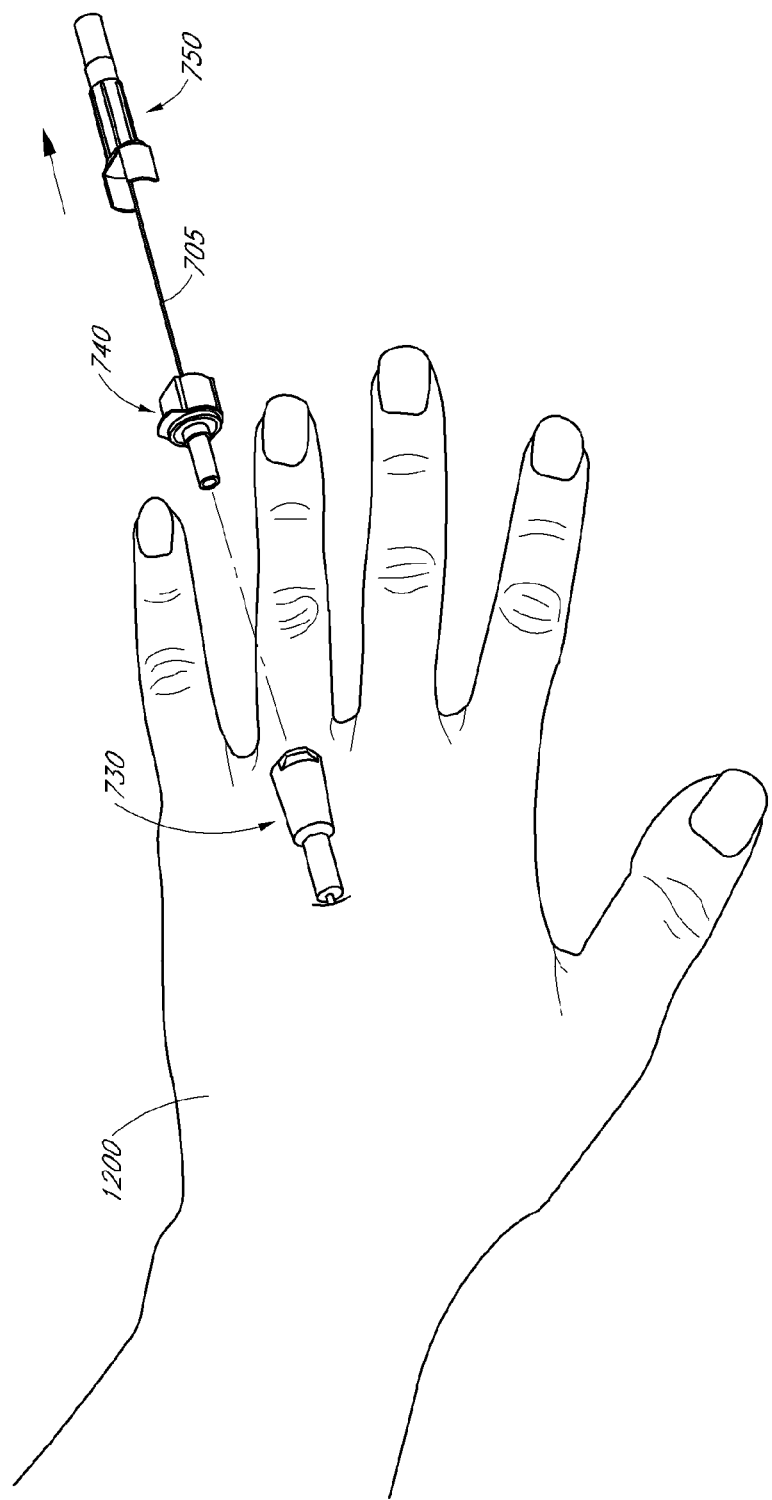
FIG. 15 is another perspective view of the medical article of FIG. 10 being used with a patient.
Figure 16:
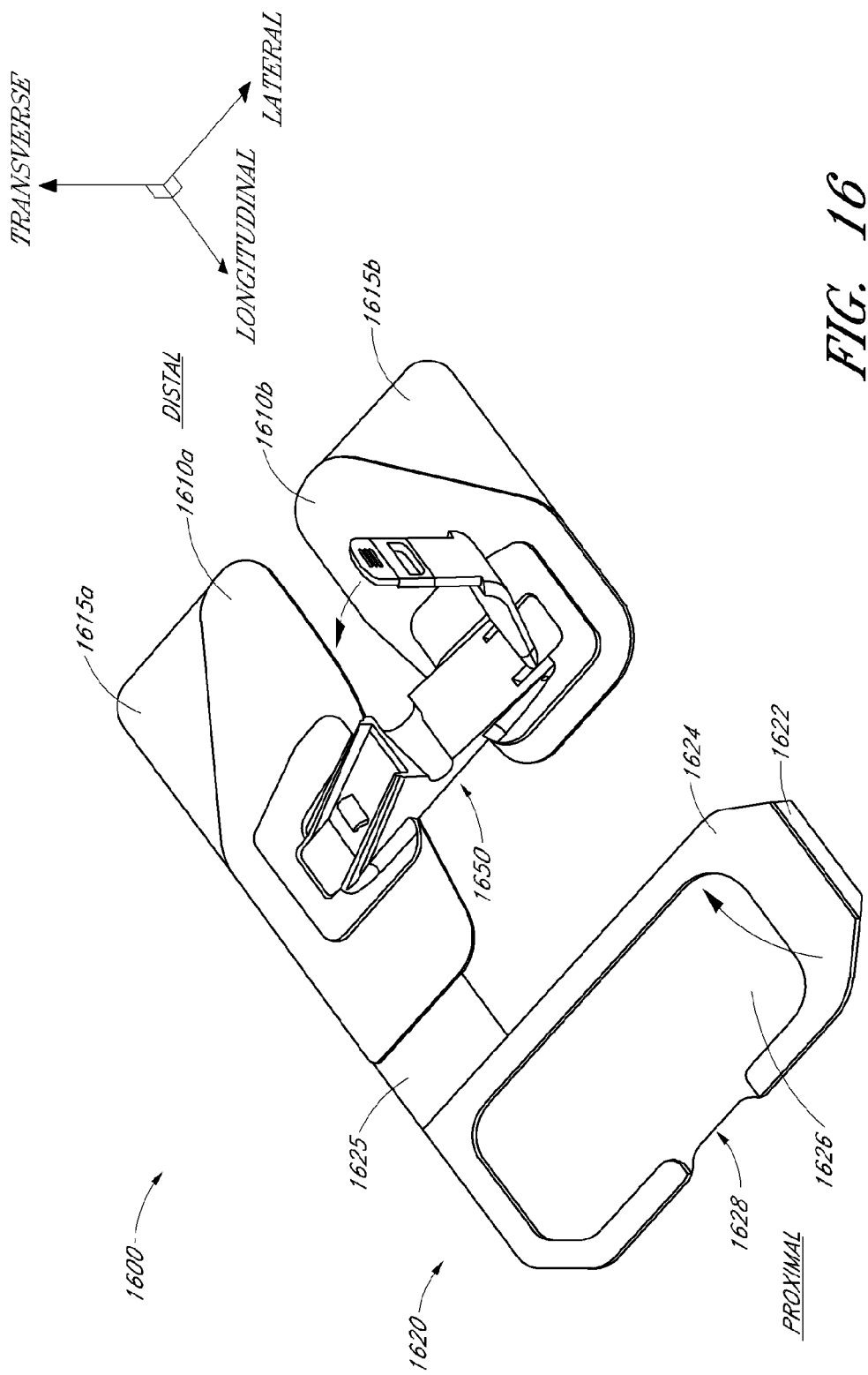
FIG. 16 is a perspective view of another embodiment of a securement device having an integral strap and dressing.

FIGS. 12-17 illustrate a method of using the catheter assembly 700 and the securement device 1600 shown in FIG. 16 in the context of starting a peripheral I.V. line. The discussion of this embodiment and this example method of use are meant to augment the description of the invention above and both should be read together.

Figure 12:
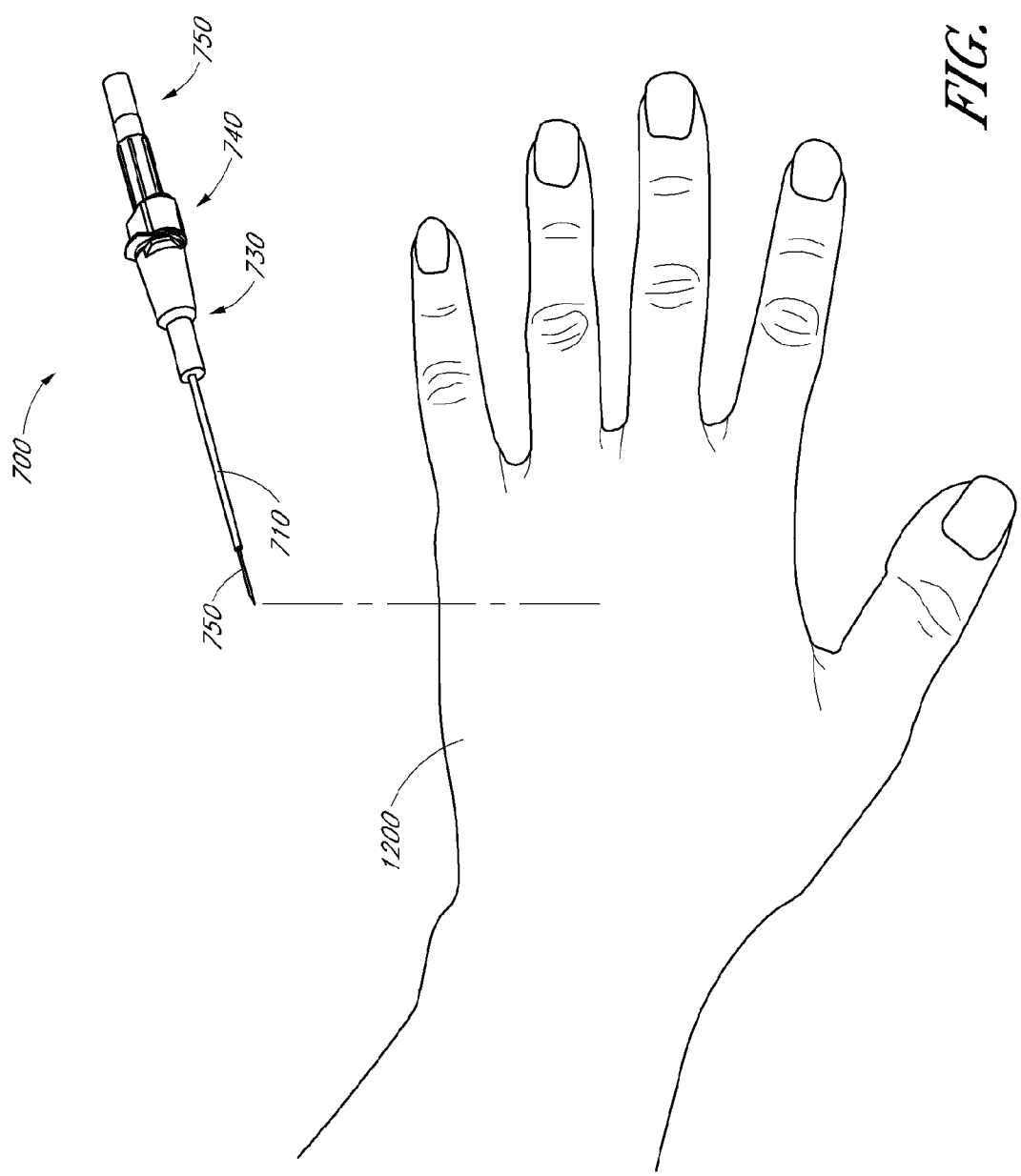
FIG. 12 is another perspective view of the medical article of FIG. 10.
Figure 13:
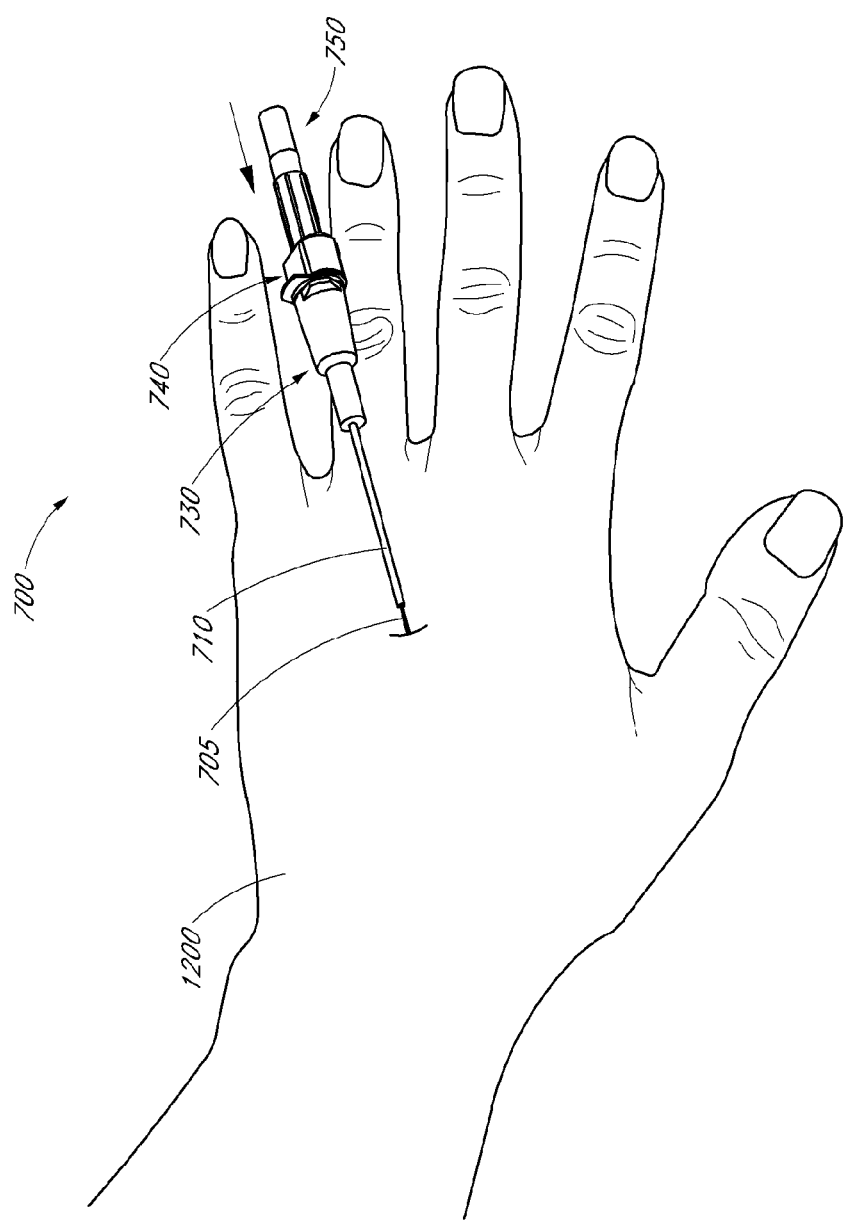
FIG. 13 is a perspective view of the medical article of FIG. 10 being used with a patient.

In starting a peripheral I.V. line, the medical provider begins by positioning the catheter assembly 700 over the hand 1200 of a patient as shown in FIG. 12. The method continues in FIG. 13 by inserting the introducer needle 705 into the vasculature of the hand 1200. The catheter 710 can follow the introducer needle 705 into the vasculature as the introducer needle 705 is advanced proximally.

Turning to FIG. 14, the introducer needle 705 is removed by pulling on flash chamber assembly 750 and moving the flash chamber assembly 750 in a distal direction. The flash chamber assembly 750 separates from the tip protector 740 under a sufficient force in the distal direction. The introducer needle 705 is coupled to the flash chamber assembly 750. Thus, as the flash chamber assembly 750 is withdrawn distally, the introducer needle 705 is also withdrawn distally through the catheter 710 and tip protector 740 as illustrated.

The method continues in FIG. 15 as the flash chamber assembly 750 is moved further distally. As shown, when the proximal tip portion of the introducer needle 705 is withdrawn into the tip protector 740, the tip protector 740 engages the proximal tip portion of the introducer needle 705. Thus, the proximal end of the introducer needle 705 becomes coupled to the tip protector 740. The tip protector 740 then separates from the catheter hub 730 as the flash chamber assembly 750 is moved further distally from the insertion site.

The medical provider can then attach a connector to the catheter hub 730 to establish fluid communication between the catheter hub 730 and a medical line. The connector can be configured to attach to a medical article for carrying fluids to or from the catheter 710, for example to a catheter extension set. The connector may therefore be formed with a lumen extending therethrough along a generally longitudinal axis in order to carry the fluids. In the illustrated embodiment, the connector is configured with a female luer-lock connection fitting to accept the male luer-lock connection fitting 738 disposed on the catheter hub 730. In some embodiments, the connector comprises a vented one-way valve.

With reference now to FIG. 16, an embodiment of a securement device 1600 includes anchor pads 1610a and 1610b, a dressing 1620, and a retainer 1650. The anchor pads 1610a and 1610b and retainer 1650 may all be configured similar to the embodiments described above with respect to FIG. 1. The anchor pads 1610a and 1610b may also include release liners 1615a and 1615b similar to or the same as release liners 115a and 115b. The retainer 1650 may comprise materials similar to those described above with respect to the retainer 200. Similarly, the retainer 1650 may be formed as a single unit, or may be formed as several different elements and integrated together.

In the illustrated embodiment, the dressing 1620 is covered by a release liner 1621. The release liner 1621 may be configured similar to the release liner 121 described with respect to FIG. 1. The dressing 1620 has an adhesive surface 1624 and an occlusive layer 1626. The adhesive surface 1624 and occlusive layer 1626 can be configured similar to the adhesive surface 124 described with respect to FIG. 1. However, in contrast to the adhesive surface 124 described with respect to FIG. 1, the adhesive surface 1624 of the dressing 1620 is not disposed over the surface of an occlusive layer 1626 of the dressing 1620. Of course, the adhesive surface 1624 may instead be disposed over the entire surface of the occlusive layer 1626 of the dressing 1620, for example in any of the ways described above with respect to the adhesive surface 124 and the occlusive layer 126. The release liner 1621 covers the adhesive surface 1624 and can be removed prior to applying the adhesive surface to, for example, the skin of a patient. As shown, similar to FIG. 1, the adhesive surface 1624 and release liner 1621 do not cover an edge 1622 of the dressing to form a tab as described above.

The dressing 1620 may otherwise be configured similar to the dressing 120 described with respect to FIG. 1. However, the attachment of the dressing 1620 to the anchor pad 110a may be configured differently than the attachment of the dressing 120 to the anchor pad 110a. In FIG. 16, the dressing 1620 of the securement device 1600 is attached to the rear portion of anchor pad 110b by a flap 1625. The flap 1625 can comprise the same or similar materials as the anchor pad 110a and/or occlusive layer 1626. The dressing 1620 can fold over the flap 1625 as the dressing 1620 is rotated about the flap 1625 towards the distal direction.

Figure 17:
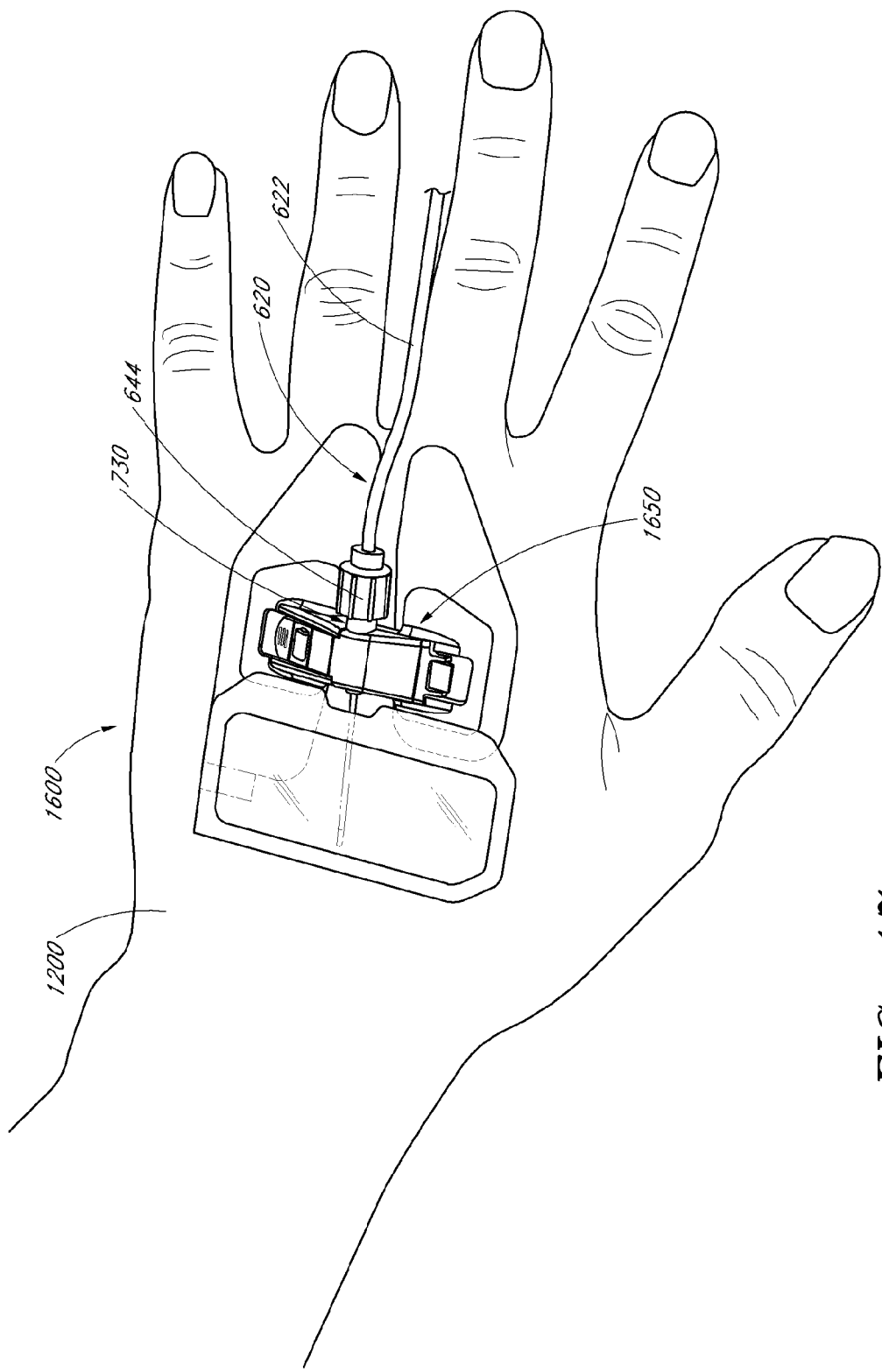
FIG. 17 is a top view of the securement device of FIG. 16 secured to a patient with the dressing folded against the patient with the retainer in the closed position.

The method of using the securement device 1600 is shown as completed in FIG. 17. The catheter hub 730 is coupled to extension set 620 by screwing the spin nut 644 onto the catheter hub 730 before or after the securement device 1600 is attached to the hand and before or after the catheter hub 730 is secured and stabilized by the retainer 1650. The securement device 1600 is attached to the hand by removing the release liners 1615a and 1615b from the anchor pads 1610a and 1610b to expose the lower adhesive surface of the anchor pads 1610a and 1610b, and placing the anchor pads 1610a and 1610b on the hand. The catheter hub 730 secured by the retainer by positioning at least a portion of the catheter hub 730 into the channel of the retainer 1650, closing the strap over the channel, and securing the strap with the retention mechanism as discussed above.

The release liner 1624 of the dressing 1620 may be removed to expose the adhesive surface. The dressing 1620 is folded down over the insertion site and adhered to the skin of the patient, as shown in FIG. 17. At this point, the catheter 610, catheter hub 730, and tube 622, are all secured to the securement device 1600, and are stabilized on the patient. The medical provider may then introduce fluids or medicaments into the catheter 610 for administration to the patient.

It is to be noted that the figures provided herein are not drawn to any particular proportion or scale, and that many variations can be made to the illustrated embodiments. Those of skill in the art will recognize that the disclosed aspects and features shown herein are not limited to any particular embodiment of a stabilization system, and stabilization systems that include one or more of the features herein described can be designed for use with a variety of medical articles.

The various embodiments of the stabilization systems described above in accordance with the present invention thus provide a means to releasably secure a connector fitting or extension set to a patient. An insertion site of a catheter attached to the connector fitting or extension set may be covered with an integrated dressing.

Of course, it is to be understood that not necessarily all objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

Furthermore, the skilled artisan will recognize the interchangeability of various features from different embodiments. In addition to the variations described herein, other known equivalents for each feature can be mixed and matched by one of ordinary skill in this art to construct stabilization systems and techniques in accordance with principles of the present invention.

Although this invention has been disclosed in the context of certain embodiments and examples, it will be understood by those skilled in the art that the present invention extends beyond the specifically disclosed embodiments to other alternative embodiments and/or uses of the invention and obvious modifications and equivalents thereof. Thus, it is intended that the scope of the present invention herein disclosed should not be limited by the particular disclosed embodiments described above.

What is claimed is:

1. A securement device for securing a catheter, comprising:
   a first anchor pad and a second anchor pad, wherein a gap separates an edge of the first anchor pad from an adjacent edge of the second anchor pad;
   a retainer comprising:
      a first base member secured to an upper surface of the first anchor pad;
      a second base member secured to an upper surface of the second anchor pad; and a body coupled to the first base member and the second base member, wherein a portion of the body spans the gap separating the first anchor pad from the second anchor pad, the portion of the body including an open channel through an upper surface of the body, the open channel aligned with the gap, the body comprising a first securement mechanism and a second securement mechanism; and a strap having a first end rotatably coupled to the body to transition the strap between an open position and a closed position, wherein in the closed position:
the strap covers the open channel, and
a second end of the strap opposite of the first end engages both the first securement mechanism and the second securement mechanism.

2. The securement device according to claim 1, further comprising a dressing attached to the first anchor pad, the dressing configured to move independently of the strap between an open configuration and a closed configuration.

3. The securement device according to claim 2, wherein a proximal end of the first anchor pad extends a first length proximal of a proximal end of the second anchor pad, wherein the dressing is attached to the first anchor pad along the first length.

4. The securement device according to claim 3, wherein the dressing is configured to rotate or fold from an uncovered position to a covered position, and wherein the dressing is proximal of the body of the retainer in the covered position.

5. The securement device according to claim 4, wherein the dressing is attached to the first length along a score line.

6. The securement device according to claim 2, wherein a portion of the dressing includes an adhesive surface, and wherein a release liner covers the adhesive surface.

7. The securement device according to claim 6, wherein the release liner includes a coating selected from the group consisting of an anti-microbial, an anti-bacterial, an anti-hemorrhagic agent, and combinations thereof.

8. The securement device according to claim 1, wherein the first securement mechanism is a locking tab extending from a surface of the body, wherein the second end of the strap includes an opening, and wherein the locking tab passes through the opening in the closed position of the strap.

9. The securement device according to claim 8, wherein:
the second securement mechanism comprises continuous protrusions on opposing edges of the body,
the second end of the strap has a width less than a distance between the opposing edges of the body,
the locking tab is positioned between the opposing edges of the body, and
the second end of the strap is positioned between the continuous protrusions in the closed position of the strap.

10. The securement device according to claim 1, wherein the body of the retainer comprises a first angled support and a second angled support separated by the open channel, wherein the first angled support is coupled to the first base member and the second angled support is coupled to the second base member.

11. The securement device according to claim 10, wherein:
the first end of the strap is rotatably coupled to the second angled support,
the first securement mechanism is a locking tab extending from a surface of the first angled support,
the second end of the strap includes an opening, and
the locking tab passes through the opening in the closed position of the strap.

12. The securement device according to claim 11, wherein:
the second securement mechanism comprises continuous protrusions on opposing edges of the first angled support,
the second end of the strap has a width less than a distance between the opposing edges of the first angled support,
the locking tab is positioned between the opposing edges of the first angled support, and
the second end of the strap is positioned between the continuous protrusions in the closed position of the strap.

13. The securement device according to claim 1, wherein the first base member, the second base member, and the body are a single integral piece.

14. The securement device according to claim 1, wherein the strap comprises an elastomeric material that conforms to an outer surface of the catheter in the closed position of the strap.

15. The securement device according to claim 1, wherein the retainer includes an exterior abutment surface to prevent movement of the catheter in the open channel.

16. The securement device according to claim 15, wherein the exterior abutment surface comprises an upper abutment surface and a lower abutment surface.

17. The securement device according to claim 1, wherein the strap includes a first strap section and a second strap section, the second strap section having a thickness less than a thickness of the first strap section.

18. The securement device according to claim 17, wherein the first strap section is attached to the second strap section via a hinge.

19. The securement device according to claim 18, wherein the first strap section includes an indentation with a curvilinear shape at the hinge.

20. The securement device according to claim 1, wherein the open channel narrows from a first width to a second width smaller than the first width.

* * * * *